United States Patent
Nozato

(10) Patent No.: US 10,052,018 B2
(45) Date of Patent: Aug. 21, 2018

(54) WAVEFRONT MEASURING METHOD FOR ADAPTIVE OPTICS SYSTEM

(71) Applicant: CANON KABUSHIKI KAISHA, Tokyo (JP)

(72) Inventor: Koji Nozato, Rochester, NY (US)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/092,073

(22) Filed: Apr. 6, 2016

(65) Prior Publication Data
US 2017/0290507 A1 Oct. 12, 2017

(51) Int. Cl.
| A61B 3/14 | (2006.01) |
| A61B 3/10 | (2006.01) |
| A61B 3/12 | (2006.01) |
| G02B 27/00 | (2006.01) |
| A61B 3/15 | (2006.01) |

(52) U.S. Cl.
CPC .............. *A61B 3/1015* (2013.01); *A61B 3/12* (2013.01); *A61B 3/158* (2013.01); *G02B 27/0068* (2013.01)

(58) Field of Classification Search
CPC ......... A61B 3/1015; A61B 3/158; A61B 3/12; G02B 27/0068
USPC ........................................ 351/206, 205, 200
See application file for complete search history.

(56) References Cited

U.S. PATENT DOCUMENTS

| 6,120,450 A | 9/2000 | Li |
| 6,890,076 B2 | 5/2005 | Roorda |
| 7,530,692 B2 * | 5/2009 | Yamaguchi .......... A61B 3/1015 351/206 |
| 7,665,844 B2 | 2/2010 | Chen et al. |
| 8,087,779 B2 | 1/2012 | Levecq |
| 8,591,029 B2 | 11/2013 | Nozato |
| 8,684,526 B2 | 4/2014 | Neal |
| 8,936,364 B2 | 1/2015 | Porter et al. |

(Continued)

OTHER PUBLICATIONS

Eugénie Dalimier, Adaptive Optics Correction of Ocular Higher-Order Aberrations and the Effects on Functional Vision, Aug. 2007, Thesis, Department of Experimental Physics, National University of Ireland, Galway, IR, 2007.

(Continued)

*Primary Examiner* — Tuyen Tra
(74) *Attorney, Agent, or Firm* — Canon U.S.A., Inc. IP Division

(57) ABSTRACT

A method, a controller, and a non-transitory medium for controlling an optical-image pickup apparatus. Receiving quality data representative of quality of wavefront data. Comparing the quality data to a threshold. Performing normal adaptive optics feedback if the wavefront data is of sufficient quality. Performing an initial adjustment if the wavefront data is not of sufficient quality. The initial adjustment comprising sending control information to modify the optical path in which light is radiated onto a subject. After the initial adjustment, receiving new quality data that is based on new wavefront data after the optical path has been modified. Performing the normal adaptive optics feedback if the quality information indicates that the wavefront data is of sufficient quality. Re-performing the initial adjustment if the new quality information indicates that the wavefront data is not of sufficient quality.

25 Claims, 14 Drawing Sheets

(56) References Cited

U.S. PATENT DOCUMENTS

| | | | |
|---|---|---|---|
| 8,955,970 | B2 | 2/2015 | Nozato |
| 8,971,363 | B2 | 3/2015 | Levecq et al. |
| 8,992,017 | B2 | 3/2015 | Yuasa |
| 9,016,861 | B2 | 4/2015 | Nozato et al. |
| 9,044,174 | B2 | 6/2015 | Nozato et al. |
| 9,107,619 | B2 | 8/2015 | Nozato et al. |
| 2014/0104618 | A1 | 4/2014 | Potsaid et al. |
| 2014/0176907 | A1* | 6/2014 | Nozato ............... A61B 3/1015 351/206 |
| 2014/0247425 | A1 | 9/2014 | Hammer et al. |
| 2015/0150450 | A1 | 6/2015 | Nozato |

OTHER PUBLICATIONS

Martin J. Booth, Adaptive Optics in Microscopy, Author's Manuscript, 2011, Oxford, UK, 2011.
Richard Legras, Hélène Rouger, Calculations and Measurements of the Visual Benefit of Correcting the Higher-Order Aberrations Using Adaptive Optics Technology, Journal of Optometry, Jul.-Sep. 2008, 1(1):22-29, Spanish Council of Optometry, Madrid, ES, 2008.
Ramkumar Sabesan, Kamran Ahmad, Geunyoung Yoon, Correcting Highly Aberrated Eyes Using Large-Stroke Adaptive Optics, Journal of Refractive Surgery, Nov. 1, 2007, 23(9):947-952, SLACK Incorporated, Thorofare, NJ, 2007.
H. Hofer, L. Chen, G. Y. Yoon, B. Singer, Y. Yamauchi, D. R. Williams, Improvement in Retinal Image Quality with Dynamic Correction of the Eye's Aberrations, Optics Express, May 21, 2001, 8(11):631-643,Optical Society of America, Washington DC, 2001.
Junzhong Liang, David R. Williams, and Donald T. Miller, Supernormal Vision and High Resolution Retinal Imaging through Adaptive Optics, Journal of the Optical Society of America A, Nov. 1997, 14(11):2884-2892, Optical Society of America, Washington DC, 1997.
Pablo Artal, Javier Santamaría, Julian Bescós, Retrieval of the Wave Aberration of the Human Eyes from Actual Point-Spread Function Data, Journal of the Optical Society of America A, Aug. 1988, 5(8)1201-1206, Optical Society of America, Washington DC, 1988.
J. Santamaría, P. Artal, J. Bescós, Determination of the Point-Spread Function of Human Eyes Using a Hybrid Optical-Digital Method, Journal of the Optical Society of America A, Jun. 1, 1987, 4(6):1109-1114, Optical Society of America, Washington DC, 1987.
Konrad Pesudovs, Katrina E. Parker, Han Cheng, Raymond A. Applegate, The Precision of Wavefront Refraction Compared to Subjective Refraction and Autorefraction, Optometry and Vision Science, May 2007, 84(5):387-392, American Academy of Optometry, Orlando, FL, 2007.
Yan Zhang, Barry Cense, Jungtae Rha, Ravi S. Jonnal, Weihua Gao, Robert J. Zawadzki, John S. Werner, Steve Jones, Scot Olivier, Donald T. Miller, High-Speed Volumetric Imaging of Cone Photoreceptors with Adaptive Optics Spectral-Domain Optical Coherence Tomography, Optics Express, May 15, 2006, 14(10):4380-4394, Optical Society of America, Washington DC, 2006.
Andreas W. Dreher, Josef F. Bille, Robert N. Weinreb, Active Optical Depth Resolution Improvement of the Laser Tomographic Scanner, Applied Optics, Feb. 15, 1989, 28(4):804-808, Optical Society of America, Washington DC, 1989.
Junzhong Liang, Bernhard Grimm, Stefan Goelz, Josef F. Bille, Objective Measurement of Wave Aberrations of the Human Eye with the Use of a Hartmann-Shack Wave-Front Sensor, Journal of the Optical Society of America A, Jul. 1, 1994, 11(7)1949-1957, Optical Society of America, Washington DC, 1994.
Yue Zhou, Kim K. Y. Cheung, Sigang Yang, P. C. Chui, Kenneth K. Y. Wong, Ultra-Widely Tunable, Narrow Linewidth Picosecond Fiber-Optical Parametric Oscillator, IEEE Photonics Technology Letters, Dec. 1, 2010, 22(23):1756-1758, IEE, Piscataway, NJ, 2010.

* cited by examiner

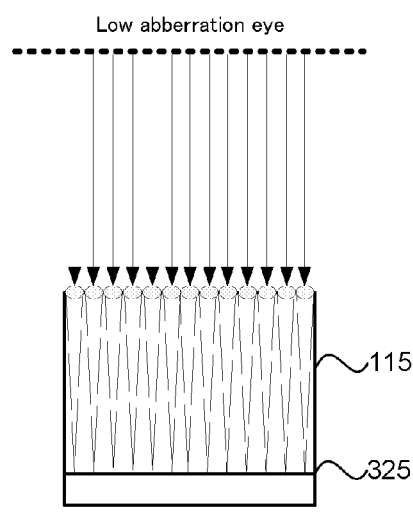
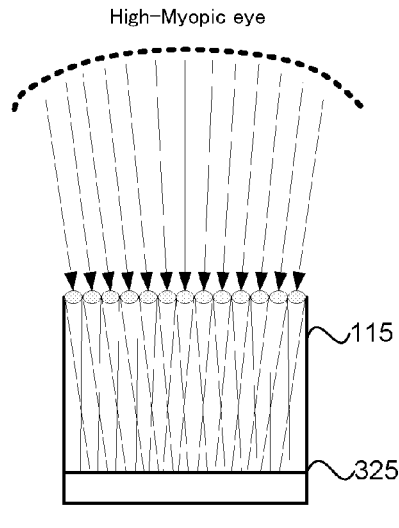
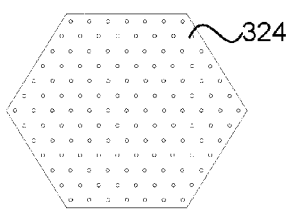
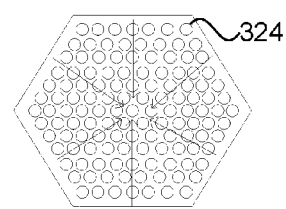
FIG. 3A
FIG. 3B
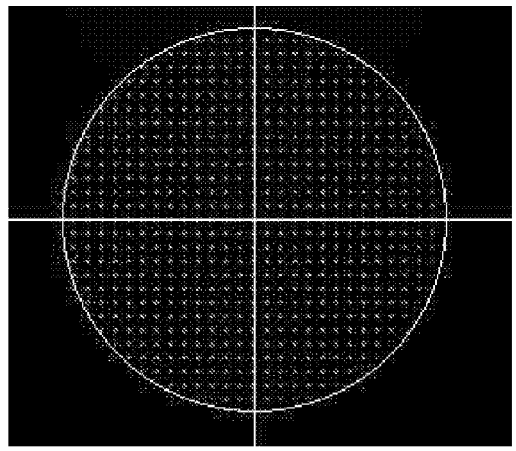
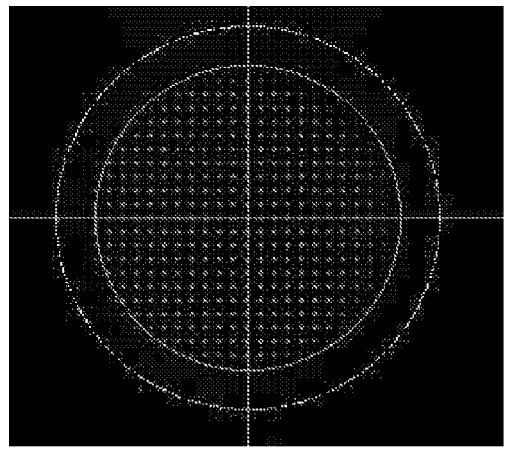
FIG. 4A
FIG. 4B
FIG. 4C
FIG. 4D

WAVEFRONT MEASURING METHOD FOR ADAPTIVE OPTICS SYSTEM

BACKGROUND

Field of Art

The present disclosure relates to a system and method for controlling an adaptive optics system used for imaging a fundus.

Description of the Related Art

Ophthalmoscopes, ophthalmic image pickup apparatuses, fundus imaging systems such as: scanning laser ophthalmoscopes (SLOs) that irradiate the fundus with a laser in two dimensions; and optical coherence tomographs (OCTs) that utilizes the interference of low coherence light have been developed and commercialized. Thus, SLOs and OCTs have become important tools for the study of the human fundus in both normal and diseased eyes.

The resolution of such ophthalmic image pickup apparatuses has recently been improved by, for example, achieving high NA of irradiation laser light. However, when an image of the fundus is to be acquired, the image must be acquired through optical tissues including the cornea and the crystalline lens. As the resolution increases, the aberrations of the cornea and the crystalline lens have come to significantly affect the quality of acquired images.

AO-SLO and AO-OCT in which the adaptive optics (AO) are a correction optical system that measures the aberration of the eye and corrects for the aberration have been pursued to improve the resolution of these systems. The AO-SLO and AO-OCT generally measure the wavefront of the eye using a Shack-Hartmann wavefront sensor system. A deformable mirror or a spatial-phase modulator is driven to correct the measured wavefront, and an image of the fundus is acquired, thus allowing AO-SLO and AO-OCT to acquire high-resolution images.

SUMMARY

A method for controlling an optical-image pickup apparatus configured to radiate measurement light onto a subject, to measure a wavefront aberration generated at the subject with a wavefront measurement device, to correct the aberration with a wavefront correction device, and to acquire an optical image of the subject. The method comprises receiving a first set of quality data that is representative of a quality of wavefront data. Wherein the wavefront data is an estimation of wavefront aberrations generated at the subject. The method further comprises comparing the first set of quality data to a first threshold.

In a first case wherein the comparison of the first set of quality information indicates that the wavefront data is of sufficient quality then performing normal adaptive optics feedback. The normal adaptive optics feedback comprising sending a first set of control information to the optical-image pickup apparatus instructing the optical-image pickup apparatus to compensate for aberrations based on an estimated shape of the wavefront based on the received wavefront data. The normal adaptive optics feedback further comprising re-estimating the shape of the wavefront based on re-acquired wavefront data and sending a new first set of control information to the optical-image pickup apparatus instructing the optical-image pickup apparatus to compensate for aberrations based on the re-estimated shape of the wavefront.

In a second case wherein the comparison of the first set of quality information indicates that the wavefront data is not of sufficient quality then performing an initial adjustment. The initial adjustment comprising sending a second set of control information to the optical-image pickup apparatus instructing the optical-image pickup apparatus to modify the optical path in which measurement light is radiated onto the subject. The initial adjustment further comprising receiving a new first set of quality data that is based on new wavefront data after the optical path has been modified. The initial adjustment further comprising re-comparing the new first set of quality data to the first threshold.

In a third case wherein the comparison of the first set of quality information indicates that the wavefront data is of sufficient quality then performing the normal adaptive optics feedback in which the optical path has been adjusted based on the second set of control information.

In a fourth case wherein the comparison of the first set of quality information indicates that the wavefront data is not of sufficient quality then re-performing the initial adjustment based on a new second set of control information.

The method described above, wherein before receiving the first set of quality data the wavefront correction unit compensates for the known optical aberrations based on optical prescription data associated with the subject.

The method described above, wherein modifying the optical path include adjusting a position of a second correction unit other than the wavefront correction unit.

The method described above, wherein: a second correction unit includes as least one or more focusing optical components selected from a group including a lens and a mirror; and the second set of control information includes instructions for the optical-image pickup apparatus to move the at least one or more focusing optical components.

The method described above, wherein the wavefront correction device is one of a deformable mirror or a spatial light phase modulator.

The method described above, wherein the wavefront measurement device is a Shack-Hartman sensor that detects a plurality of Hartmann spots.

The method described above, wherein the first set of quality data is based on a numerical count of the plurality of Hartmann spots.

The method described above, wherein the first set of quality data is based on a plurality of diameters of the plurality of Hartmann spots.

The method described above, wherein the first set of quality data is based on signal intensity data of the plurality of Hartmann spots.

The method described above, wherein the normal adaptive optics feedback is done repeatedly so as to form a feedback loop.

The method described above, further comprising controlling the image pickup apparatus so as to acquire the optical image of the subject by scanning a spot in parallel with continuous use of the normal adaptive optics feedback.

The method described above, wherein the initial adjustment is performed repeatedly until the comparison of the first set of quality information with the first threshold indicates that the wavefront data is of sufficient quality and controlling the image pickup apparatus so as to acquire the optical image of the subject by scanning a spot in parallel with continuous use of the normal adaptive optics feedback after the comparison of the first set of quality information with the first threshold indicates that the wavefront data is of sufficient quality.

The method described above, wherein the initial adjustment is performed repeatedly, wherein the initial adjustment includes: a first part of modifying the optical path by adjusting a position of one or more focusing optical components to change the focus until the comparison of the first set of quality information with the first threshold indicates that the wavefront data is of sufficient quality; and a second part, of modifying the optical path by adjusting a position of one or more focusing optical components to change the astigmatism until the comparison of the first set of quality information with a second threshold indicates that the wavefront data is of sufficient quality. The method described above also further comprises controlling the image pickup apparatus so as to acquire the optical image of the subject by scanning a spot in parallel with continuous use of the normal adaptive optics feedback after the comparison of the first set of quality information with the first threshold and the second threshold indicates that the wavefront data is of sufficient quality.

The method described above, wherein: the first set of quality data includes multiple elements which represent different qualitative aspects of the wavefront data; the first threshold include multiple elements which provide different thresholds for different qualitative aspects of the wavefront data; and comparing the first set of quality data to the first threshold includes comparing those elements of the first set of quality data associated with particular qualitative aspects of the wavefront data with thresholds associated with those qualitative aspects of the wavefront data.

A non-transitory computer readable medium encoded with instructions for performing the method described above.

A controller for controlling an optical-image pickup apparatus in accordance with the method described above. The controller including a processor and a memory for performing the steps of the method described above.

An apparatus comprising: the optical-image pickup apparatus and the controller described above.

BRIEF DESCRIPTION OF THE DRAWINGS

The accompanying drawings, which are incorporated in and constitute a part of the specification, illustrate exemplary embodiments.

FIGS. 3A-B are generalized illustrations of a wavefront sensor and Hartmann spots as might be used in an embodiment.

FIGS. 4A-D are illustrations wavefront spots as detected by a wavefront sensor.

DESCRIPTION OF THE EMBODIMENTS

Embodiments will be described below with reference to the attached drawings. Like numbers refer to like elements throughout. Exemplary embodiments will be described in detail with reference to the drawings below. It shall be noted that the following description is merely illustrative and exemplary in nature, and is in no way intended to limit the disclosure and its applications or uses. The relative arrangement of components and steps, numerical expressions and numerical values set forth in the embodiments do not limit the scope of the disclosure unless it is otherwise specifically stated. Techniques, methods, and devices which are well known by individuals skilled in the art may not have been discussed in detail since an individual skilled in the art would not need to know these details to enable the embodiments discussed below. Further, an image photographing apparatus as disclosed in the following which is used to inspect an eye as described below may also be used to inspect other objects including but not limited to skin, and internal organs.

Adaptive Optics

Adaptive optics systems are typically controlled using a feedback loop type system. In these AO feedback loops aberrations are measured and then the aberrations are corrected are processed one after another continuously. The wavefront measurement is the key for this feedback loop because once the wavefront is measured incorrectly, the wavefront corrector can't compensate for the real aberration and may actually generate additional aberrations. Slowing down the measurement process and possibly adding artifacts to the measurements.

Figure 1A:
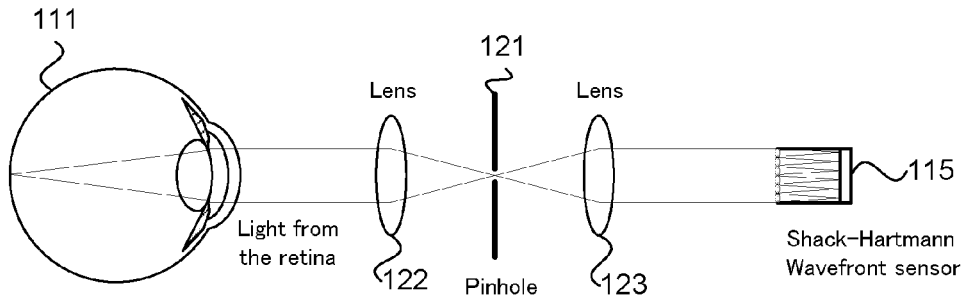
FIGS. 1A-B are generalized illustrations of a portion of system as used in an embodiment.
Figure 1B:
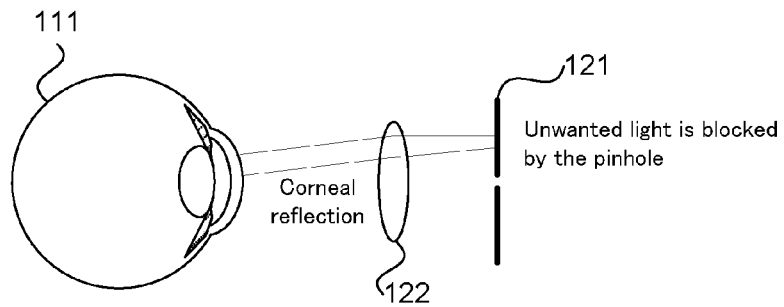

To improve the accuracy of the wavefront measurement, a pinhole is placed in front of the wavefront sensor to block light coming from surfaces other than the retina especially from the cornea. This pinhole can also block the back reflection light from other optical elements in the optical system. FIGS. 1A-B are generalized illustrations of such a system. FIG. 1A illustrates a subject 111 such as an eye being imaged by a system that includes a wavefront sensor 115. A pinhole 121 is placed between the subject 111 and the wavefront sensor 115. The pinhole 121 also placed between 2 lenses 122 and 123. The pinhole 121 is positioned between 2 lenses 122 and 123 such that extraneous light does not reach the wavefront sensor 115. The size of the pinhole is such that it blocks light from the cornea as illustrated in FIG. 1B.

Figure 2A:
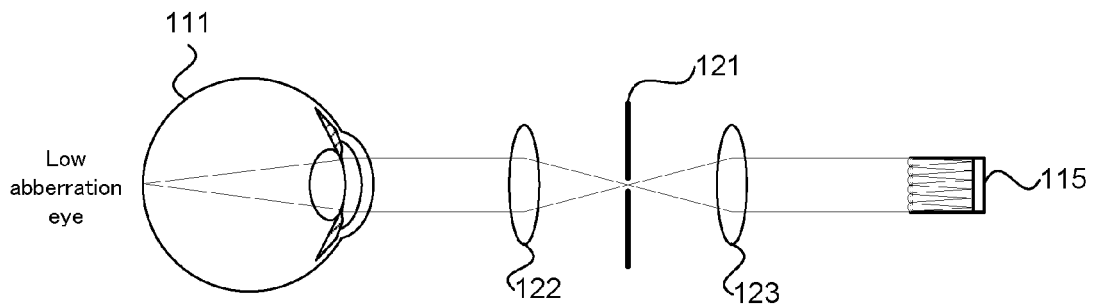
FIGS. 2A-B are generalized illustrations of a portion of system as used in an embodiment.
Figure 2B:
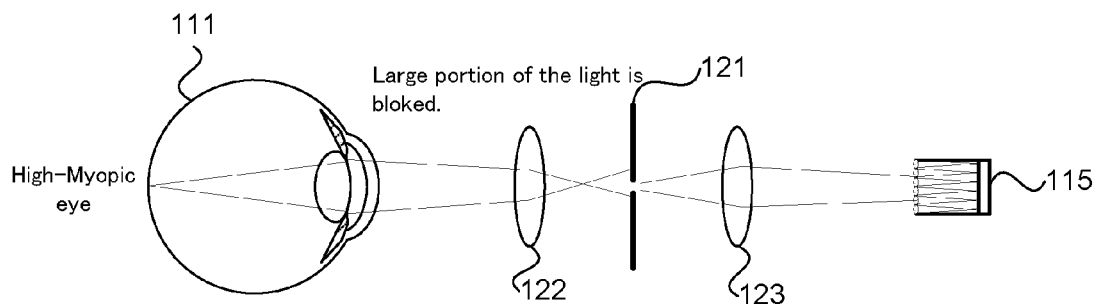

The pinhole 121 allows light to pass mainly from the retina of the subject 111 as illustrated in FIG. 1A. This pinhole 121 works efficiently with eyes whose aberration is small as illustrated in FIG. 2A, but if the eye has a large amount of aberration, large portions of the light from the retina may be blocked by the pinhole 121 as illustrated in FIG. 2B. As a result, the number of the spots on the wavefront sensor 115 decreases and the signal strength of each spot is weaker.

Light from aberrated eyes not only limits the amount of light that passes through the pinhole 121, but also has an effect on spot detection at the wavefront sensor 115. Low aberrated light from the eye can shape small spots 324 on the CCD sensor surface 325 of the wavefront sensor 115 as illustrated in FIG. 3A. When the spots 324 are small, it is easy to detect a center (or centroid) of the intensity of the spots and to calculate the shape of the wavefront. If the light is aberrated, the spots 324 get blurred, and it can be difficult to detect the center (or centroid) of the intensity as illustrated in FIG. 3B.

FIG. 4A is an illustration of a Hartmann image from a normal eye and a white target illustrating an estimated location of the pupil based on the Hartmann image. FIG. 4B is an illustration of a Hartmann image from a myopic eye and a grey target illustrating an estimated location of the pupil based on the Hartmann image, and a white target illustrating a relative location of the illumination beam based upon the system alignment. FIG. 4C is a zoomed in image of 9 spots from the Hartmann image of a normal eye. FIG. 4D is a zoomed in image of 9 spots from the Hartmann image of a myopic eye.

Problems associated with making wavefront measurements such as identifying the center of a blurred spot can make the measurements incorrect. As the measured aberration data is not correct, the AO feedback may never achieve a well corrected status if the AO control starts with such an incorrect measurement. In other words, the AO control can fall into a false minimum if the initial control data is very far off from the ideal system. The applicant has determined that the AO feedback control loop should not start with the aberration data calculated from these abnormal conditions.

Ophthalmoscope

A first embodiment is described with reference to a fundus image photographing apparatus (ophthalmoscope) such as the photographing apparatus illustrated in FIG. 5.

Embodiments are directed towards systems, methods, non-transitory computer readable medium, and software which are used in connection with an imaging system such as an ophthalmoscope 100. FIG. 5 is an illustration of an exemplary ophthalmoscope 100. An ophthalmoscope 100 is a system or apparatus for obtaining information about an interior portion of the eye 111 (e.g., the fundus).

An exemplary embodiment may be a scanning ophthalmoscope. A scanning ophthalmoscope scans a spot across the eye 111. The spot may be a spot of light from a light source 101 that is scanned across the eye 111.

In an exemplary embodiment 100, the spot of light is produced by a light source 101. The light source 101 may be incorporated into the ophthalmoscope 100; alternatively, the ophthalmoscope 100 may include an input for receiving the light source 101. The input for the light source 101 may be a fiber optic input 102 or a free space input (not shown). The light source 101 may be a laser, a broadband light source, or multiple light sources. In an exemplary embodiment, the light source 101 is a super luminescent diode (SLD) light source having a wavelength of 840 nm. The wavelength of the light source 101 is not particularly limited, but the wavelength of the light source 101 for fundus image photographing is suitably set in a range of approximately 800 nm to 1,500 nm in order to reduce glare perceived by a person being inspected and to maintain imaging resolution.

In an exemplary embodiment, light emitted from the light source 101 passes through a single-mode optical fiber 102, and is radiated as collimated light (measuring light 105) by a collimator 103.

In an exemplary embodiment, the polarization of the irradiated light may be adjusted by a polarization adjusting member 119 (not shown) provided in a path of the single-mode optical fiber 102. In an alternative configuration, the light source 101 is polarized and single-mode optical fiber 102 is polarization maintaining fiber. In another configuration, the polarization adjusting member may be placed after the collimator 103. Alternatively, the polarization adjusting member may be replaced with a polarizer. In an alternative embodiment, the irradiated light may be unpolarized, depolarized, or the polarization may be uncontrolled.

The measuring light 105 radiated from the collimator 103 passes through a light division portion 104 including a beam splitter. An exemplary embodiment includes an adaptive optical system.

The adaptive optical system may include a light division portion 106, a wavefront sensor 115, wavefront adjustment device 108, a pinhole 121, lens 122, lens 123, and reflective mirrors 107-1 to 107-4 for guiding the measuring light 105 to and from those components. The reflective mirrors 107-1 to 107-4 are provided to guide the measuring light 105 to and from the pupil of an eye 111, the wavefront sensor 115, and the wavefront adjustment device 108. The reflective mirrors may be replaced with suitable optics, such as lenses and/or apertures. Likewise, the lenses may be replaced with mirrors. The wavefront sensor 115 and the wavefront adjustment device 108 may be in an optically conjugate relationship. A beam splitter may be used as the light division portion 106. The wavefront sensor 115 may be a Shack-Hartmann sensor or other type of sensor that gathers information that is representative of the wavefront of light coming from the subject.

A pinhole 121 may be placed between the wavefront sensor 115 and the beam splitter 106. A lens 122 may be placed between the beamsplitter 106 and the pinhole 121. A lens 123 may be placed between the pinhole 106 and the wavefront sensor 115. The pinhole 121, lens 122, and lens 123 are arranged to ensure that light from the surface of the retina is detected by the wavefront sensor 115 while other light is blocked. Lenses 122-123 may be replaced with mirrors.

The measuring light 105 passing through the light division portion 106 is reflected by the reflective mirrors 107-1 and 107-2 so as to enter the wavefront adjustment device 108. The measuring light 105 is reflected by the wavefront adjustment device 108 and is further reflected by the reflective mirrors 107-3 and 107-4.

The wavefront adjustment device 108 maybe a transmissive device or a reflective device. The wavefront adjustment device 108, may be an addressable spatial light phase modulator that allows relative phases across a beam coming into the wavefront adjustment device 108 to be adjusted such that relative phases across the beam coming out of the wavefront adjustment device 108 are adjustable. In an exemplary embodiment, one or two spatial phase modulators including a liquid crystal element is used as the wavefront adjustment device 108. The liquid crystal element may modulate a phase of only a specific polarized component. In which case, two liquid crystal elements may be employed to modulate substantially orthogonal polarized components of the measuring light 105. In an alternative embodiment, the wavefront adjustment device 108 is a deformable mirror.

The measuring light 105 reflected off mirror 107-4 is two-dimensionally scanned by a scanning optical system 109. In an exemplary embodiment, the scanning optical system 109 includes a first scanner 109-1 and a second scanner 109-2. The first scanner 109-1 rotates around the first axis, while the second scanner 109-2 rotates around a second axis. The first axis is substantially orthogonal to the second axis. Substantially in the context of the present disclosure means within the alignment and measurement tolerances of the system. The scanning optical system 109 may include one or more additional scanners 109-3 (not shown) which are used for steering the scanning area to different parts of the fundus.

Figure 5:
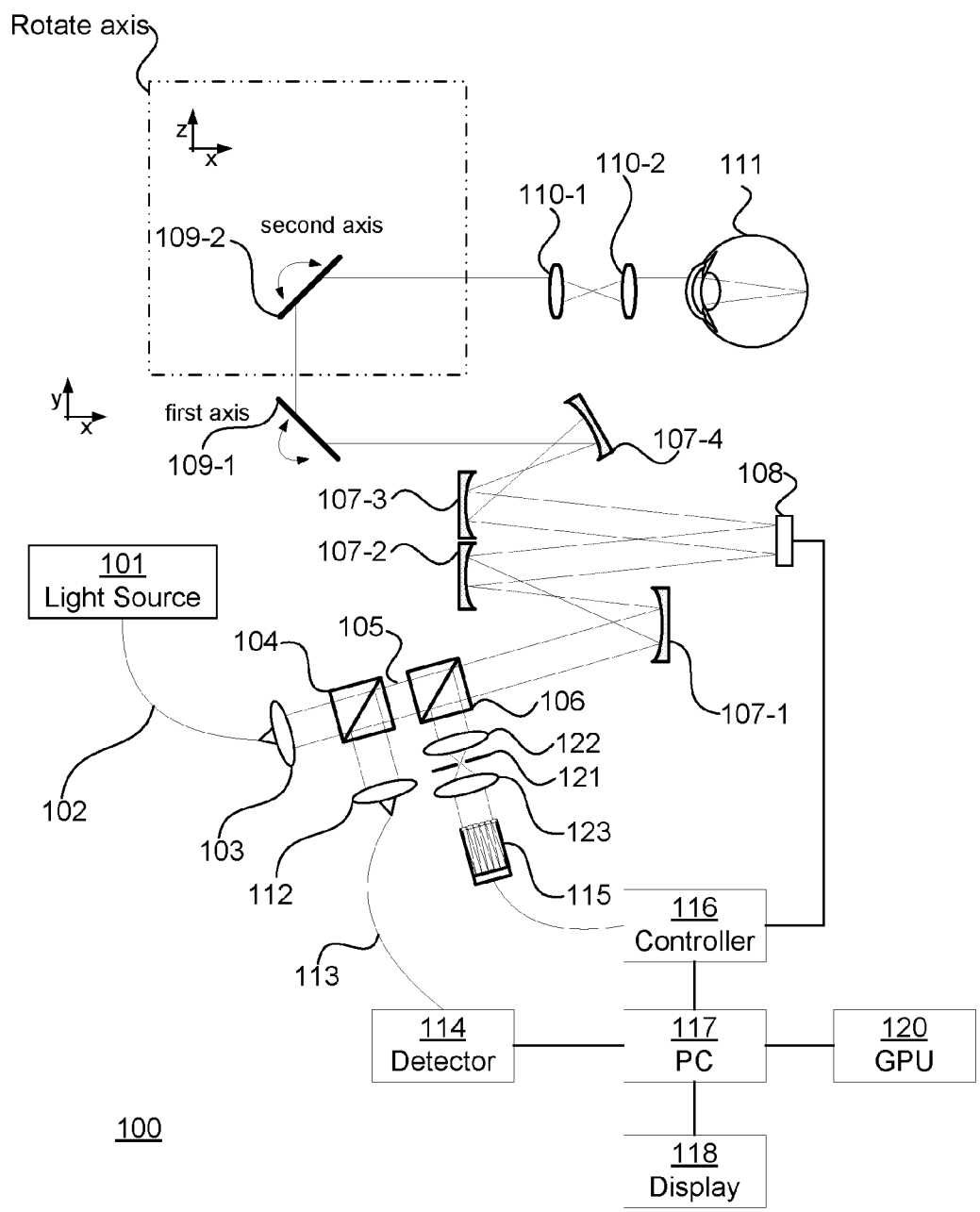
FIG. 5 is an generalized illustration of an apparatus in which an embodiment may be implemented.

FIG. 5 illustrates the first scanner 109-1 rotating in the x-y plane, while the second scanner 109-2 is rotating in the z-x plane. In the context of the present disclosure, rotating the measuring light 105 in a first plane around the first axis is equivalent to rotating the measuring light 105 in the first plane and is equivalent to scanning the spot of light in the main scanning direction or the lateral direction of the object being imaged. In the context of the present disclosure, rotating the measuring light 105 in a second plane around the second axis is equivalent to scanning the spot of light in the sub-scanning direction or the longitudinal direction of the object being imaged. The sub-scanning direction is substantially orthogonal to the main scanning direction.

A scanning period of the first scanner 109-1 is less than the scanning period of the second scanner 109-2. The order of the first scanner 109-1 and the second scanner 109-2 may be exchanged without impacting the operation of an exemplary embodiment. The first scanner 109-1 may operate in a resonant scanning mode.

In an exemplary embodiment, the scanning optical system 109 may be a single tip-tilt mirror that is rotated around the first axis and around the second axis that is substantially orthogonal to the first axis. An exemplary embodiment may also use non-mechanical beam steering techniques.

In an exemplary embodiment, the first scanner 109-1 and the second scanner 109-2 are galvano-scanners. In another exemplary embodiment, one of the first scanner 109-1 and the second scanner 109-2 is a resonant scanner. The resonant scanner may be used for the main scanning direction. The resonant scanner may be tuned to oscillate at a specific frequency. There may be additional optical components, such as lenses, mirrors, apertures, and etc. between the scanners 109-1, 109-2, and other optical components. These additional optical components may be arranged such that the light is focused onto the scanners, in a manner that is optically conjugate with all of or one or more of the subject 111, the wavefront adjustment device 108, the wavefront sensor 115, and a detector 114.

The measuring light 105 scanned by the scanning optical system 109 is radiated onto the eye 111 through eyepieces 110-1 and 110-2. The measuring light radiated to the eye 111 is reflected, scattered, or absorbed by the fundus 111. When the eyepieces 110-1 and 110-2 are adjusted in position, suitable irradiation may be performed in accordance with the diopter of the eye 111. Lenses may be used for the eyepiece portion in this embodiment, but other optical components such as spherical mirrors may also be used.

Light which is produced by reflection, fluorescence, and/or scattering by a fundus of the eye 111 then travels in the reverse direction along the same path as the incident light. A part of the reflected light is reflected by the light division portion 106 to the wavefront sensor 115 to be used for measuring a light beam wavefront.

In an exemplary embodiment, a Shack-Hartmann sensor is used as the wavefront sensor 115. However, an exemplary embodiment is not limited to a Shack-Hartmann sensor. Another wavefront measurement unit, for example, a curvature sensor may be employed or a method of obtaining the wavefront by reverse calculation from the spot images may also be employed.

In FIG. 5, when the reflected light passes through the light division portion 106, a part thereof is reflected on the light division portion 104 and is guided to a light intensity sensor 114 through a collimator 112 and an optical fiber 113. The light intensity sensor 114 converts the light into an electrical signal. The electrical signal is processed by a PC 117 or other suitable processing device into an image of the subject and the image is displayed on a display 118.

The wavefront sensor 115 is connected to an adaptive optics controller 116. The received wavefront is transferred to the adaptive optics control unit 116. The wavefront adjustment device 108 is also connected to the adaptive optics control unit 116 and performs modulation as instructed by the adaptive optics control unit 116. The adaptive optics controller 116 calculates a modulation amount (correction amount) to obtain a wavefront having less aberration based on the wavefront obtained by a measuring result of the wavefront sensor 115, and instructs the wavefront adjustment device 108 to perform the modulation according to the modulation amount. The wavefront measurement and the instruction to the wavefront adjustment device are repeated and a feedback control is performed so as to obtain a suitable wavefront.

In an exemplary embodiment the light division portions 104 and/or 106 are fused fiber couplers. In an alternative exemplary embodiment, the light division portions 104 and/or 106 may include partially reflective mirrors. In another alternative exemplary embodiment, the light division portions 104 and/or 106 may include dichroic reflectors, in which case a different wavelength of light is used for obtaining an image of the fundus then is used for detecting the spatial phase image that controls the adaptive optics system.

The detector 114 may detect reflections or fluorescence associated with the scanning spot. The detection system may make use confocal microscopy techniques in which an aperture associated with the scanning spot is used to increase the resolution and/or contrast of the detection system.

The adaptive optics system described above includes at least the wavefront sensor 115 and the wavefront adjustment device 108 so that the aberration of the subject's eyes can be measured and compensated for. A deformable mirror (DM) or a spatial light phase modulator (SLM) can be used as the wavefront adjustment device 108. Since the typical SLM has a large number of actuators, it can modulate wavefront more precisely than DM can. A liquid crystal on silicon spatial light modulator (LCOS-SLM) may be used as the wavefront adjustment device 108. The LCOS-SLM 108 can be controlled to provide a precise spatial modulation of the phase of the beam that is used to illuminate the subject.

Myopic, Hyperopic, and Astigmatism are major aberration of the eyes and these aberration cause problems. But an AO system cannot compensate for these aberrations with wavefront sensing data because the wavefront sensing data is not correct. In an embodiment, these large aberrations are corrected before the start of a normal AO feedback loop. Once these large aberrations are corrected, the normal AO feedback loop can execute.

General Ophthalmoscope Operating Method

Figure 6:
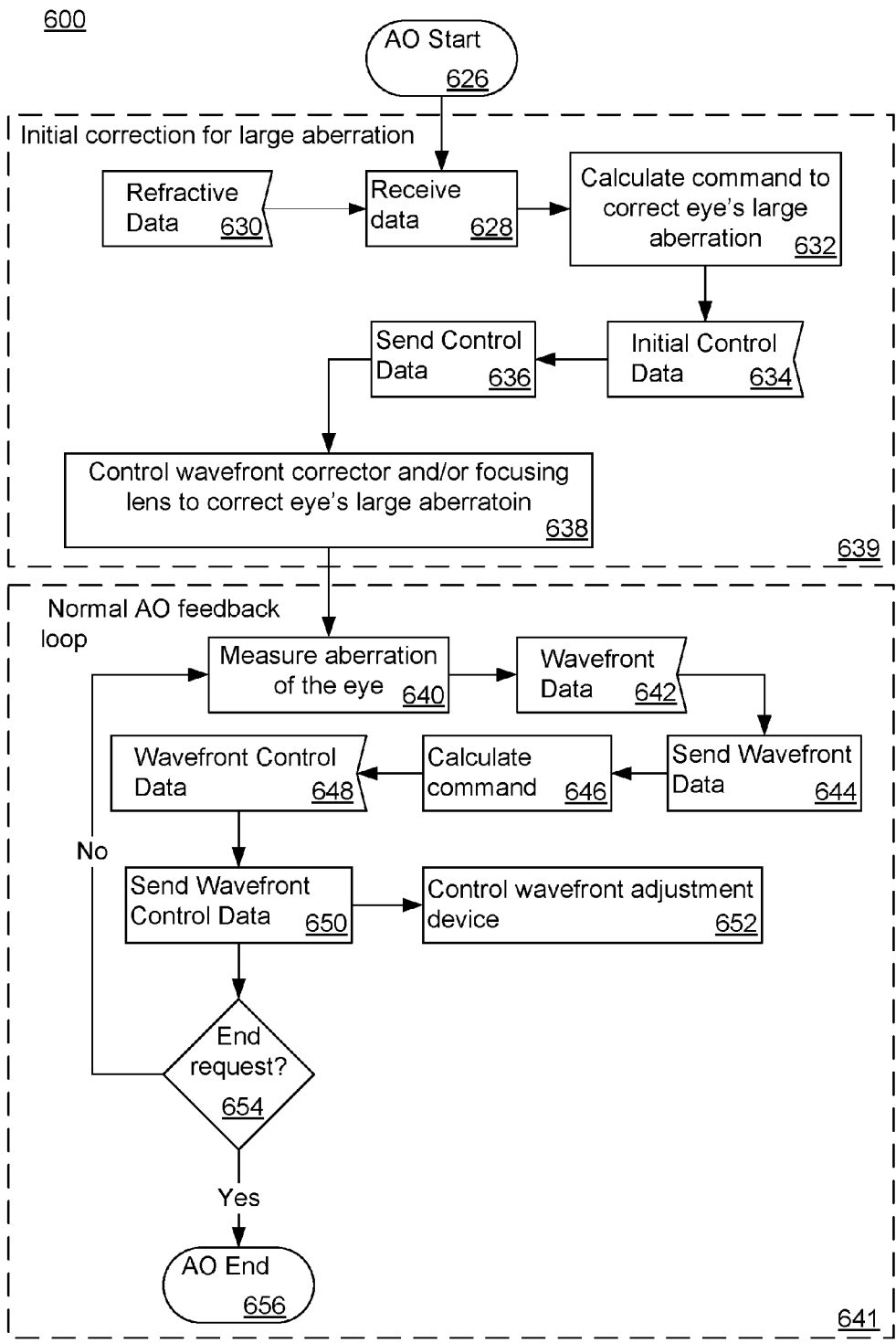
FIG. 6 is an illustration of a method that may be implemented in an embodiment.

FIG. 6 is an illustration of a method 600 for operating an ophthalmoscope that uses adaptive optics. An example of such an ophthalmoscope is ophthalmoscope 100 illustrated in FIG. 5. The method 600 may be implemented on the PC 117 and/or controller 106. The method 600 may start with a step 626 that may include receiving instructions to start the adaptive optics subroutine. Step 626 may be based upon receiving instructions from an operator via software, a hardware switch, or a sensor A step 628 may include receiving data such as refractive data 630. The refractive data 630 may include eyeglass prescription data such as sphere, cylinder, and axis of an eye 111 being inspected by the ophthalmoscope 100. Alternatively, the refractive data 630 may be a broader qualitative description of the subject's refractive error. Examples of such a qualitative descriptions are: Myopic; Hyperopic; and Astigmatism. The refractive data 630 may be entered by an operator or obtained from a database. The refractive data 630 may include any information that represents the known static aberrations that the eye 111 introduces to measurements of the subject's fundus.

The method 600 may include a step 632 may include calculating a command that corrects for the eye's 111 larger aberrations as represented by the refractive data 630. The command calculated in the step 632 may result in initial control data 636. A step 634 may include sending the initial control data 636 to the ophthalmoscope 100 to compensate for aberrations represented by the refractive data 630. In one embodiment, the initial control data 636 may include general information on what aberrations to compensate for. In another embodiment, the initial control data 636 may include specific instructions to the ophthalmoscope 100 to move specific optical elements such as lenses 110 or their equivalents specific amounts to compensate for aberrations represented by the refractive data 630. In another embodiment, the initial control data 636 may include specific instructions to the ophthalmoscope 100 to adjust the wavefront adjustment device 108 to compensate for aberrations represented by the refractive data 630.

A step 638 may include having the ophthalmoscope 100 compensate for the aberrations by controlling the wavefront adjustment device 108, specific elements such as lenses 110, their equivalent, and/or a specific focusing lens. The method 600 may be divided into two sections a first section 639 that includes steps 628-638 in which an initial correction for large aberration is done, and a second section 641 in which Normal OA feedback is performed.

The second section 641 of method 600 may include a step 640 that includes measuring the aberration of the eye 111 with the wavefront sensor 115 to produce wavefront data 642. The wavefront data 642 may include: the shape of the wavefront measured by the wavefront sensor 115; information that is used to calculate the shape of the wavefront; and/or any additional information that is generated by the wavefront sensor 115. Calculating the shape of the wavefront may include identifying a center of each Hartmann spot, estimating an offset of the center of each Hartmann spot relative to an ideal center of the Hartman spot for a perfectly flat wavefront, estimating the gradient of the wavefront based on the offset, and estimating the shape of the wavefront based on the estimated gradient of the wavefront. The center location of each Hartmann spot may be based on a weighted average, a centroid, a median value, a peak value, or a peak of a curve fitted to the data.

The method 600 may include a step 644 of sending the wavefront data 644 from the ophthalmoscope 100 to a controller 116 and/or a PC 117. The method 600 may include a step 646 of calculating a command in which the PC or the controller calculate wavefront control data 648. The step 646 may include determining a wavefront shape as measured by the wavefront sensor 115 and then determining how the wavefront adjustment device 108 may be adjusted to compensate for the measured wavefront shape. Determining how the wavefront adjustment device 108 is to be adjusted may include but is not limited to matrix multiplication and matrix inversion operations.

The method 600 may include a step 650 of sending the wavefront control data 648 from the controller 116 and/or PC 117 to the ophthalmoscope 100 which is then used to control wavefront adjustment device 108 in a step 652. The method 600 may include a step 654 of check whether the adaptive optics feedback loop should be stopped. Reasons for why the adaptive optics feedback loop may be stopped may include: if the measurement is finished; an operator requests that the measurement be stopped; or an error condition is detected. If the AO loop is stop then it ends with step 656. If the PC 117 and/or the controller 116 determine that the AO loop 641 should continue then the process may continue on beginning again with step 640.

Second Ophthalmoscope Operating Method

Figure 7:
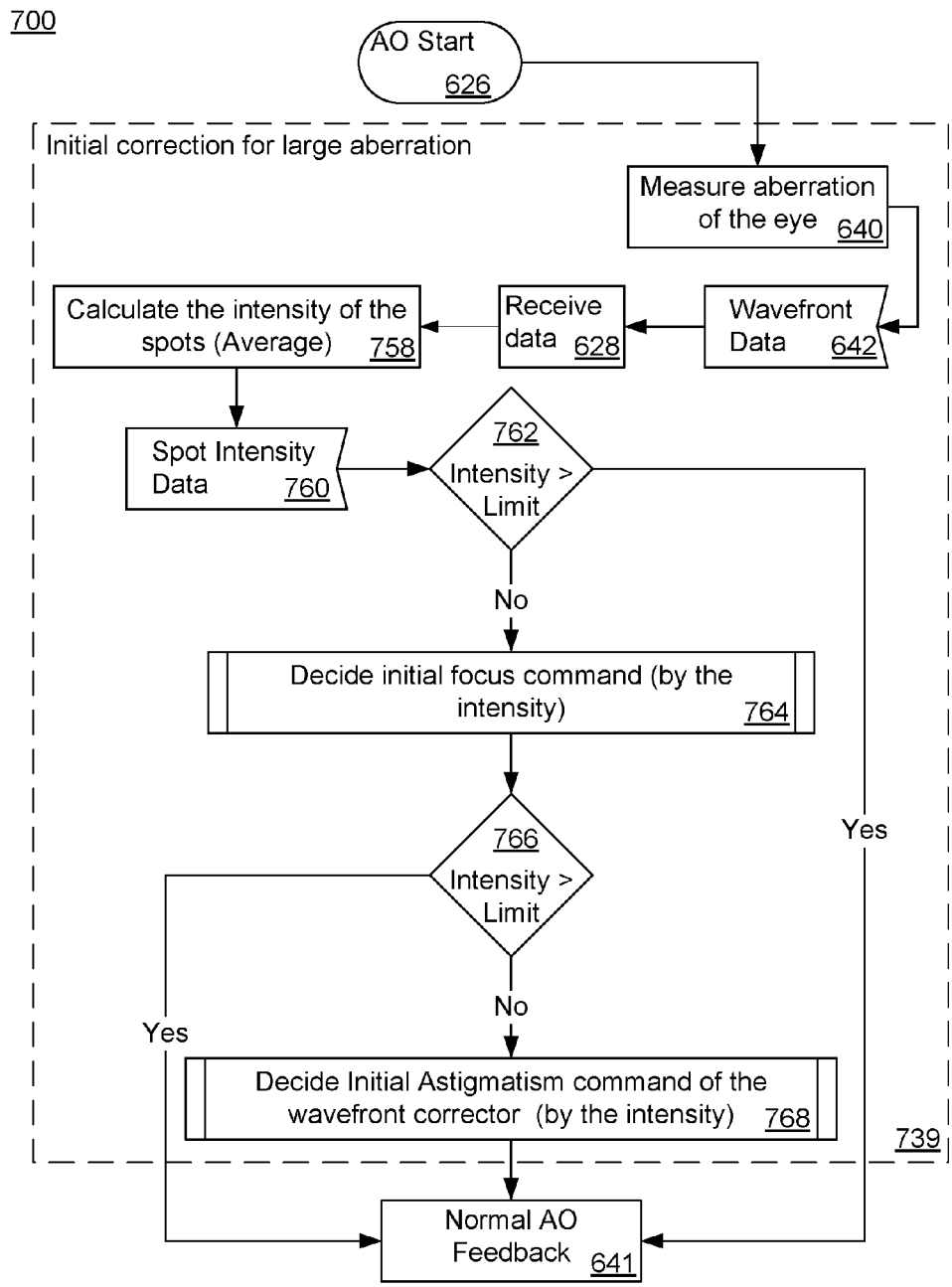
FIG. 7 is an illustration of a method that may be implemented in an embodiment.

FIG. 7 is an illustration of another method 700 for operating an ophthalmoscope that uses adaptive optics. Method 700 is similar to method 600, except that the first section 639 is replaced by a different first section 739. An example of such an ophthalmoscope is ophthalmoscope 100 illustrated in FIG. 5. The method 700 may be implemented on the PC 117 and/or controller 106. The method 700 may start with a step 626 that may include receiving instructions to start the adaptive optics subroutine.

After receiving instructions to start the adaptive optics subroutine the method 700 moves into the first section 739 of the method 700 and goes on to the step 640 that includes measuring the aberration of the eye 111 with the wavefront sensor 115 to produce wavefront data 642. The PC 117 and/or the controller 116 may then receive the wavefront data 642 in a step 628. The wavefront data 642 as obtained during this step may be equivalent to receiving the refractive data 630 or may be used to calculate an equivalent to the refractive data 630.

In a step 758, the PC 117 and/or the controller 116 may calculate the spot intensity data 760 of the Hartmann spots 324 in the wavefront data 642. The spot intensity data 760 may be a single value or a set of values and may be calculated based on the average intensity of each Hartmann spot 324 or the peak intensity of each Hartmann spot 324. The spot intensity data 760 may be calculated: as an average over all the Hartmann spots 324; an average of the average of each Hartmann spot; or an average of the peak intensity of each Hartman spot. An average intensity of all of the Hartmann spots may also be calculated. In a step 762, the PC 117 or the controller 116 may compare the spot intensity data 760 to a limit. In the step 762, the comparison may include comparing a set of values in the spot intensity data or based on the spot intensity data 760 to a set of different limits.

If the intensity is greater than the limit, then the method 700 goes on to the Normal AO feedback method 641. If the intensity is not greater than the limit, then the method 700 goes on to decide an initial focus command in a step 764 based on the spot intensity data 760. Step 764 may also include repeating steps 636-638 of sending the initial control data to the ophthalmoscope 100, and having the ophthalmoscope 100 adjust the focus based on an initial focus command.

After the focus is adjusted in step 764, the PC 117 and/or the controller 116 may recalculate the spot intensity data 760 based on new data as obtained in steps 640, 628, and 758 and re-compare the new spot intensity data 760 to a limit(s) in a step 766. The limit in the step 766 may be different from the limit in step 762. If the intensity is greater than the limit, then the method 700 goes on to the Normal AO feedback method 641. If the intensity is not greater than the limit, then the PC 117 and/or the controller 116 calculates a second set of control data which is sent to the ophthalmoscope 100 to send to the wavefront adjustment device 108 to compensate for an estimated initial astigmatism based on the spot intensity data 760 in a step 768. After the wavefront adjustment device 108 compensates for the estimated astigmatism of the subject 111 in step 768 the method goes on to Normal AO feedback method 641. In an alternative embodiment, other optical components other than the wavefront adjustment device 108 may be used to compensate for the astigmatism.

Initial Focus Sub-Method

Figure 8:
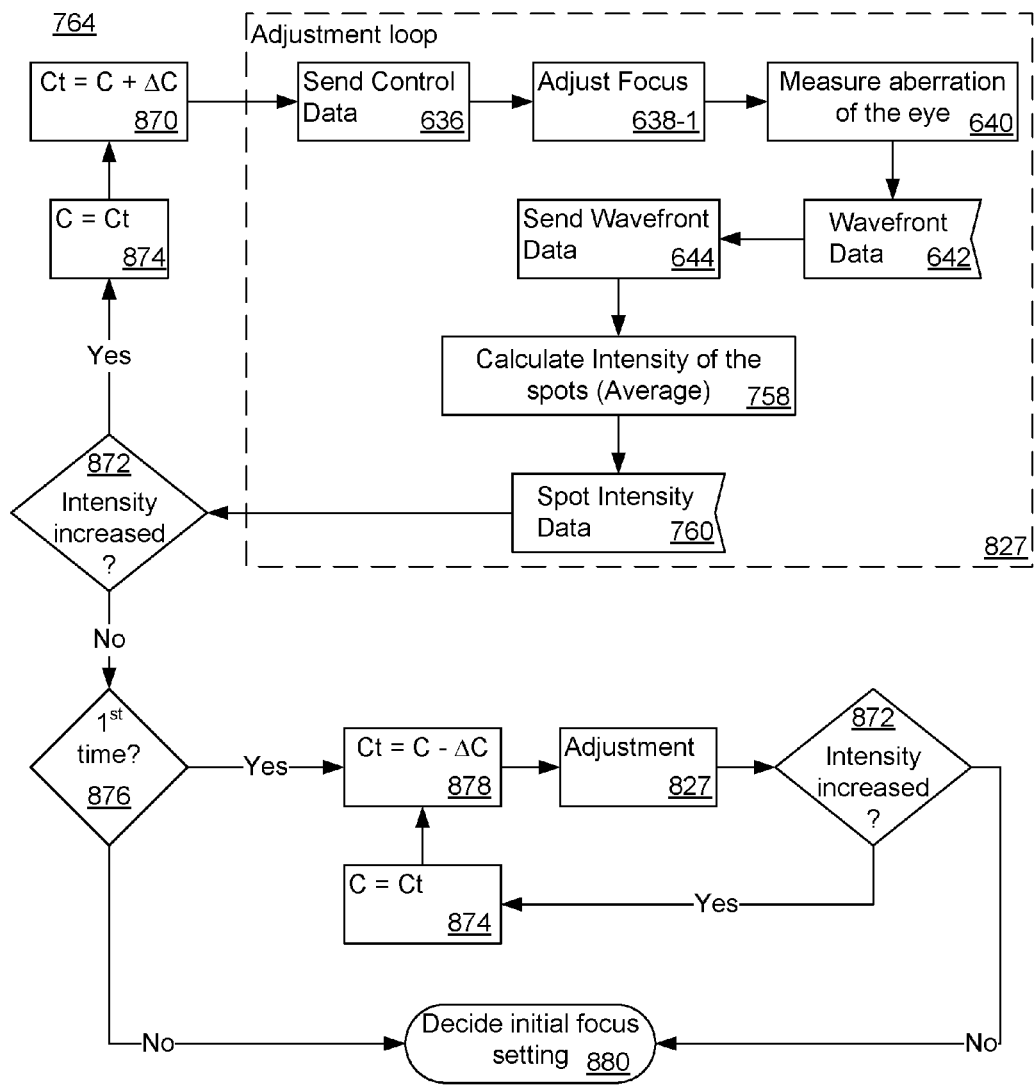
FIG. 8 is an illustration of a portion of a method that may be implemented in an embodiment.

FIG. 8 is an illustration of the sub-method 764 for deciding the initial focus command. A step 870 may include the PC 117 and/or controller 116 calculating a temporary control data (Ct) value based on equation (1).

$$Ct = C + \Delta C \quad (1)$$

In which, C is an initial control data and the offset control data $\Delta C$ is a fixed offset by which the focus is adjusted, which may be 0.1 Diopters (D). The offset control data $\Delta C$ may be another value related to the adjustment resolution of the ophthalmoscope 100. The initial setting for C may be zero, may be entered by an operator, or may be taken from a database of data associated with the subject 111 in which the value of C is based on the spherical correction of the subject's prescription. After the Ct value is calculated the sub-method 764 may enter another sub-method 827 which is an adjustment loop for adjusting the ophthalmoscope 100 and measuring the effect of that adjustment. A step 636 may include sending the control data Ct from the PC 117 and/or controller 116 to the ophthalmoscope 100. The ophthalmoscope 100 may then adjust the focus in a step 638-1 based on the control data Ct. Adjusting the focus in step 638-1 may include moving an optical element such as the focus lens 110 or their equivalent. In an alternative embodiment, adjusting the focus in step 638-1 may include adjusting the focus with the wavefront adjustment device 108. In another alternative embodiment, adjusting the focus in step 638-1 may include adjusting the focus with the wavefront adjustment device 108 and moving the focus lens 110 or their equivalent.

After the focus is adjusted in step 638-1 the sub-method 764 may include the step 640 of measuring the aberration of the eye 111 with the wavefront sensor 115 to produce wavefront data 642. The sub-method 764 may include the step 644 of sending the wavefront data 644 from the ophthalmoscope 100 to the controller 116 and/or the PC 117. In a step 758, the PC 117 and/or the controller 116 may calculate the spot intensity data 760 of the Hartmann spots 324 in the wavefront data 642. Thus, the adjustment loop may include the steps 636, 640, 644, and 758 or other methods for adjusting the state of the ophthalmoscope 100 and measuring the impact of that adjustment.

The sub method 764 may include a step 872 may include testing if the spot intensity data 760 has increased. In an alternative, a step 872 may include calculating one or more variables based on spot intensity data 760 and spot size data and determining if one or more of those values have increased. If the spot intensity data 760 has increased, then the sub-method moves on to step 874 of setting the control value C to Ct, and then repeating the step 870, the adjustment loop 827, and the decision step 872. If the spot intensity data 760 does not increase, then the sub-method 764 moves onto a step 876. In the step 876, the PC 117 and/or controller 116 checks if this is the first time step 872 (alternatively steps 870 or sub-method 827) have been performed since the sub-method 764 has started. If the answer to step 876 is no then the sub-method 764 may move on to step 880, described below.

If the answer to step 876 is yes then the sub-method 764 may move on to a step 878 in which the PC 117 and/or controller 116 calculate the temporary control data (Ct) value based on equation (2) which is similar to step 870.

$$Ct = C - \Delta C \quad (2)$$

After step 878, then the sub-method 764 may go on to perform adjustment sub-method 827 which was described above. If the spot intensity data 760 has increased, then the sub-method moves on to step 874 of setting the control value C to Ct, and then repeat step 878, adjustment sub-method 827, and step 872. If the spot intensity data 760 does not increase, then the sub-method 764 moves onto a step 880. In a step 880 the PC 117 and/or controller 116 decides the initial focus setting by resending the old control data C as in step 636 to the ophthalmoscope 100, and the ophthalmoscope 100 readjusts the focus based on the old control data C as in step 638-1. The sub-method 764 is based on a standard hill climbing optimization routine. The sub-method 764 may be implemented as a minimization optimization method instead of a maximization optimization method. The sub-method 764 may also be adapted to be a multiple variable optimization method. The sub-method 764 may be adapted to be an adaptive step size method.

Initial Focus (Astigmatism) Sub-Method

Figure 9:
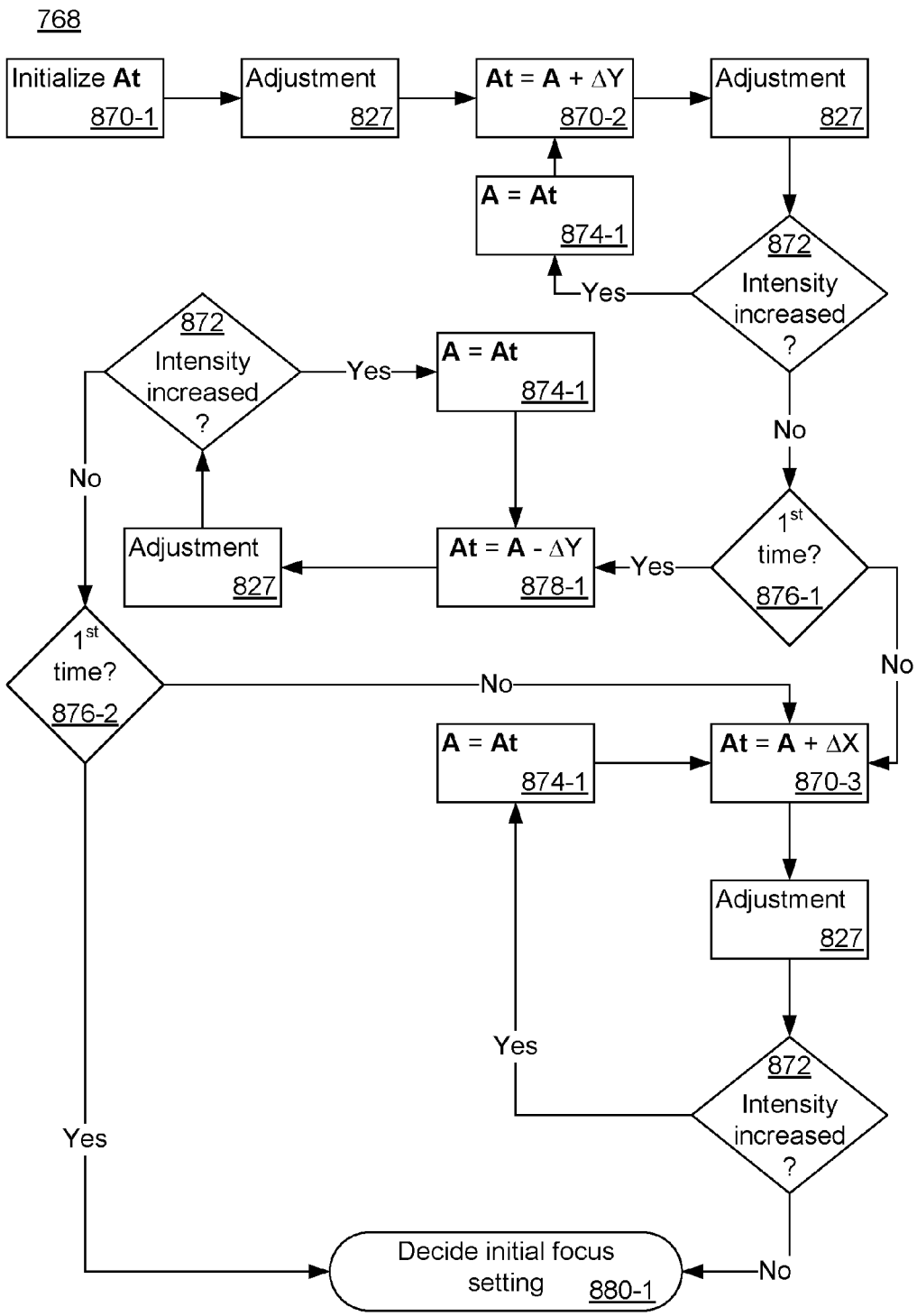
FIG. 9 is an illustration of a portion of a method that may be implemented in an embodiment.

FIG. 9 is an illustration of a sub-method 768 for deciding the initial focus command which corrects for the astigmatism. In the sub-method 768, the variables A, At, and $\Delta A$ are defined as three dimensional vectors made up of the variables (C diopters—spherical correction, X diopters—cylindrical correction, and Y degrees—axis). The initial setting for the control data A may be 0.1 D of cylindrical correction and 0 degrees of axis, may be entered by an operator, or may be taken from database of prescription data associated with the subject 111 may be set in a step. The offset control data may be described as a vector $\Delta A = \{\Delta C\ \Delta X\ \Delta y\}$. The offset control data $\Delta C$ may be redefined as 0.0D; the offset control data $\Delta X$ may be 0.1 D of cylindrical correction; and the offset control data $\Delta Y$ may be 5° of axis correction. The offset control data $\Delta A$ may be other values related to the adjustment resolution of the ophthalmoscope 100. The offset control data $\Delta C$ may be zero because the focus based on the spherical correction has been set in the sub-method 764.

The sub-method 768 may include a step 870-1 of initializing the temporary control data At for example one initial value may be: At={C 0.1D 0°}. The sub-method 768 may then move onto sub-method 827 of adjusting the focus and measuring the impact of the adjustment. After which the method may move on to step 870-2 in which the axis is adjusted according to equation (3):

$$At = A + \Delta Y \quad (3)$$

$$At = \begin{bmatrix} C \\ X \\ Y \end{bmatrix} + \begin{bmatrix} 0 \\ 0 \\ \Delta Y \end{bmatrix}$$

After the temporary control value At is calculated the sub-method 768 may then move onto sub-method 827 of adjusting the focus and measuring the effect of the adjustment. The sub method 768 may include the step 872 of testing if the spot intensity data 760 has increased. If the spot intensity data 760 has increased, then the sub-method moves on to step 874-1 of setting the control value A to At, and then repeating steps 870-2, the adjustment sub-method 827 and the test 872. If the spot intensity data 760 does not increase, then the sub-method 768 moves onto a step 876-1. In the step 876-1, the PC 117 and/or controller 116 checks if this is the first time step 870-2 has been performed since the sub-method 768 has started. If the answer to step 876-1 is no then the sub-method 764 may move on to step 870-3, described below.

If the answer to step 876-1 is yes then the sub-method 768 may move on to a step 878-1 in which the PC 117 and/or controller 116 calculate the temporary control data At based on equation (4) which is similar to step 870-2.

$$At = A - \Delta Y \quad (4)$$

$$At = \begin{bmatrix} C \\ X \\ Y \end{bmatrix} - \begin{bmatrix} 0 \\ 0 \\ \Delta Y \end{bmatrix}$$

After the temporary control value At is calculated the sub-method 768 may then move onto sub-method 827 of adjusting the focus and measuring the effect of the adjustment. The sub method 768 may include the step 872 of testing if the spot intensity data 760 has increased. If the spot intensity data 760 has increased, then the sub-method moves on to step 874-1 of setting the control value A to At, and then repeating steps 878-1, the adjustment sub-method 827 and the test 872. If the spot intensity data 760 does not increase, then the sub-method 768 moves onto a step 876-2. In the step 876-2, the PC 117 and/or controller 116 checks if this is the first time step 878-1 has been performed since the sub-method 768 has started. If the answer to step 876-2 is yes then the sub-method 764 may move on to step 880-1, described below.

If the answer to step 876-2 is no then the sub-method 768 may move on to a step 870-3 in which the PC 117 and/or controller 116 calculate the temporary control data At based on equation (5) which is similar to step 870-2.

$$At = A + \Delta X \quad (5)$$

$$At = \begin{bmatrix} C \\ X \\ Y \end{bmatrix} + \begin{bmatrix} 0 \\ \Delta X \\ 0 \end{bmatrix}$$

After the temporary control value At is calculated, the sub-method 768 may then move onto sub-method 827 of adjusting the focus and measuring the effect of the adjustment. The sub method 768 may include the step 872 of testing if the spot intensity data 760 has increased. If the spot intensity data 760 has increased, then the sub-method moves on to step 874-1 of setting the control value A to At, and then repeating steps 870-3, the adjustment sub-method 827 and the test 872. If the spot intensity data 760 does not increase, then the sub-method 768 moves onto a step 880-1. In a step 880-1 the PC 117 and/or controller 116 decides the initial focus setting by resending the old control data A as in step 636 to the ophthalmoscope 100, and the ophthalmoscope 100 readjusts the focus based on the old control data A as in step 638-1.

The sub-method 768 is based on a standard hill climbing optimization routine, taking into account the special features of eyeglass prescription data. The sub-method 768 may be implemented as a minimization optimization method instead of a maximization optimization method. The sub-method 768 may also be adapted to be a multiple variable optimization method in which both variables are adjusted at the same time. The sub-method 768 may also be adapted to an adaptive step size method. The sub-method 768 may also be adapted for negative cylinder data instead of positive cylinder data.

Method 5

Figure 10:
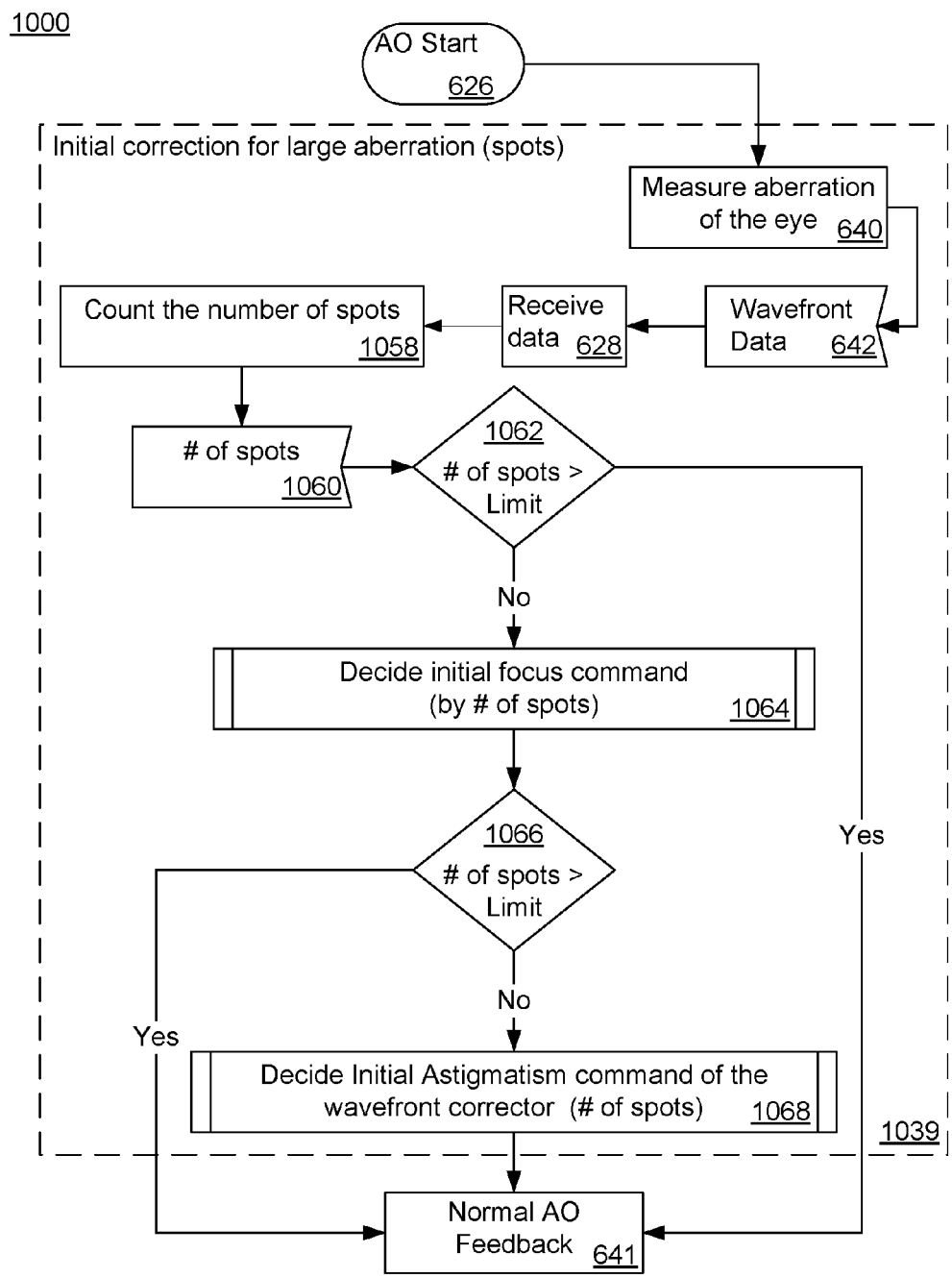
FIG. 10 is an illustration of a method that may be implemented in an embodiment.

FIG. 10 is an illustration of another method 1000 for operating an ophthalmoscope that uses adaptive optics. Method 1000 is similar to method 700, except that the metric used to make focusing decision is different.

After receiving instructions to start the adaptive optics subroutine the method 1000 into the first section 1039 of the method 1000 and go on to the step 640 that includes measuring the aberration of the eye 111 with the wavefront sensor 115 to produce wavefront data 642. The PC 117 or the controller 116 may then receive the wavefront data 642 in a step 628.

In a step 1058, the PC 117 or the controller 116 may calculate data 1060 that represents the number of Hartmann spots 324 in the wavefront data 642. In a step 1062, the PC 117 or the controller 116 may compare the number of Hartmann spots 1060 to a limit.

If the number of Hartmann spots 1060 is greater than the limit, then the method 1000 goes on to the Normal AO feedback method 641. If the number of Hartmann spots 1060 is not greater than the limit, then the method 1000 and goes on to decide an initial focus command in a step 1064 based on the number of Hartmann spots 1060. Step 1064 is similar to 764 except that the number of spots is used in the calculation instead of the intensity of spots.

After the focus is adjusted in step 1064, the PC 117 and/or the controller 116 may recalculate the number of Hartman spots 1060 based on new data as obtained in steps 640, 628, and 1058 and re-compare the new spot intensity data 1060 to a limit(s) in a step 1066. The limit in the step 1066 may be different from the limit in step 1062. If the intensity is greater than the limit(s), then the method 1000 goes on to the Normal AO feedback method 641. If the intensity is not greater than the limit, then the PC 117 and/or the controller 116 calculates a second set of control data which is sent to the ophthalmoscope 100 to send to the wavefront adjustment device 108 to compensate for an estimated initial astigmatism based on the number of Hartman spots 1060 in a step 1068. After the wavefront adjustment device 108 compensates for the estimated astigmatism of the subject 111 in step 1068 the method goes on to Normal AO feedback method 641.

Sub-Method 6

Figure 11:
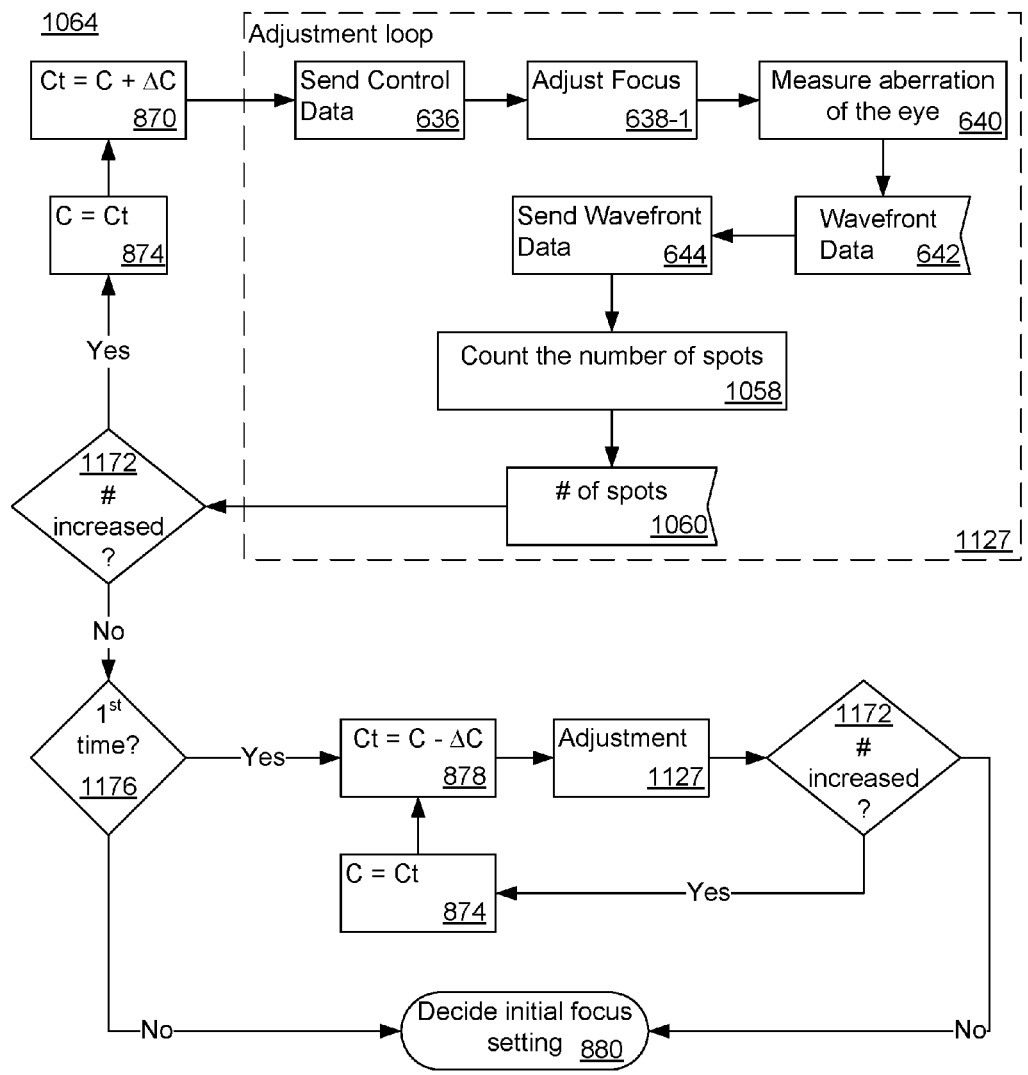
FIG. 11 is an illustration of a portion of a method that may be implemented in an embodiment.

FIG. 11 is an illustration of the sub-method 1064 for deciding the initial focus command. A step 870 may include the PC 117 and/or controller 116 calculating a temporary control data (Ct) value based on equation (1).

After the Ct value is calculated, the sub-method 1064 may enter another sub-method 1127 which is an adjustment loop for adjusting the focus and measuring the effect of that adjustment. Adjustment loop 1127 is substantially similar to adjustment loop 827. A step 636 may include sending the control data Ct. In the step 638-1 the focus is adjusted based on the control data Ct.

After the focus is adjusted in step 638-1 the sub-method 764 may include the step 640 of measuring the aberration of the eye 111 to produce wavefront data 642. The sub-method 764 may include the step 644 of sending the wavefront data 644. In a step 1058, the PC 117 and/or the controller 116 may count a number 1060 of the Hartmann spots 324 in the wavefront data 642. Thus, the adjustment loop may include the steps 636, 640, 644, and 1058 or other methods for adjusting the state of the ophthalmoscope 100 and measuring the impact of that adjustment.

The sub method 1064 may include a step 1172 of testing if the number 1060 of Hartmann spots 324 has increased. If the number 1060 has increased, then the sub-method moves on to step 874 of setting the control value C to Ct, and then repeating the step 870, the adjustment loop 1127, and the decision step 1172. If the number 1060 does not increase, then the sub-method 1064 moves onto a step 876. In the step 1176, the PC 117 and/or controller 116 checks if this is the first time step 1172 has been performed since the sub-method 1164 has started. If the answer to step 1176 is no then the sub-method 1164 may move on to step 880, described above. If the answer to step 1176 is yes then the sub-method 764 may move on to a step 878 of calculating the temporary control data (Ct) value based on equation (2).

After step 878, then the sub-method 764 may go on to perform adjustment sub-method 1127 which was described above. If the number 1060 has increased, then the sub-method 1064 moves on to step 874 of setting the control value C to Ct, and then repeating steps 878, adjustment sub-method 1127, and step 1172. If the number 1060 does not increase, then the sub-method 1064 moves onto a step 880. In the step 880 the initial focus is set by resending the old control data C as in step 636 to the ophthalmoscope 100, and the ophthalmoscope 100 readjusts the focus based on the old control data C as in step 638-1.

Sub-Method 7

Figure 12:
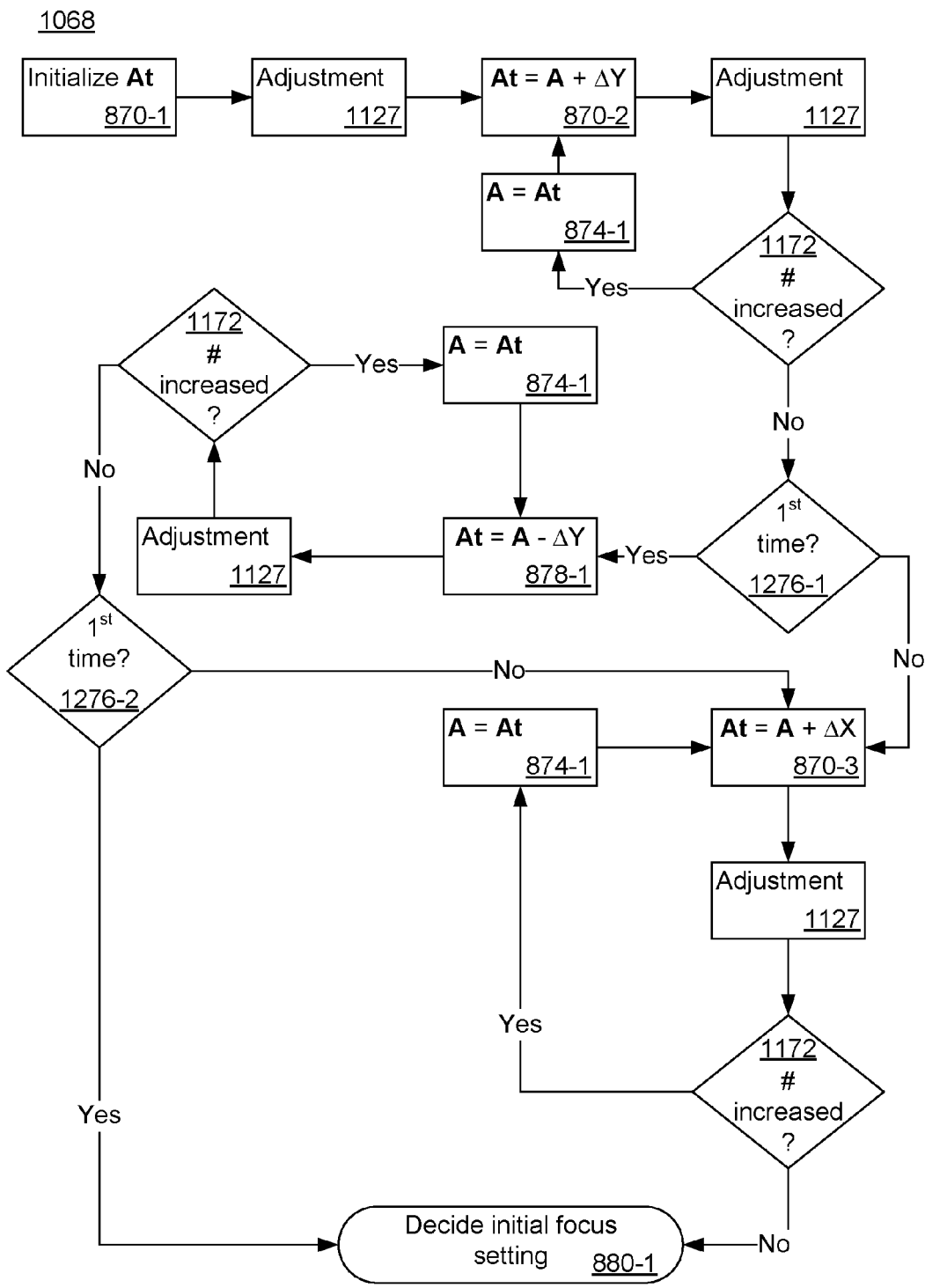
FIG. 12 is an illustration of a portion of a method that may be implemented in an embodiment.

FIG. 12 is an illustration of a sub-method 1068 for deciding the initial focus command which corrects for the astigmatism. The sub-method 1068 may include a step 870-1 of initializing the temporary control data At. The sub-method 1068 may then move onto the sub-method 1127 of adjusting the focus and measuring the impact of the adjustment. After which the method may move on to step 870-2 in which the axis is adjusted according to equation (3). After the temporary control value At is calculated the sub-method 1068 may then move onto sub-method 1127 of adjusting the focus and/or astigmatism and measuring the effect of the adjustment. The sub method 1068 may include the step 1172 of testing if the number 1060 of Hartmann spots has increased. If the number 1060 of Hartmann spots has increased, then the sub-method 1068 moves on to step 874-1 of setting the control value A to At, and then repeating steps 870-2, the adjustment sub-method 827 and the test 1172. If the spot intensity data 760 does not increase, then the sub-method 768 moves onto a step 1176-1. In the step 1276-1, the PC 117 and/or controller 116 checks if this is the first time step 870-2 has been performed since the sub-method 1068 has started. If the answer to step 1276-1 is no then the sub-method 764 may move on to step 870-3, described below.

If the answer to step 1276-1 is yes then the sub-method 1068 may move on to a step 878-1 in which the PC 117 and/or controller 116 calculate the temporary control data At based on equation (4). After the temporary control value At is calculated the sub-method 1068 may then move onto sub-method 1127 of adjusting the focus and/or astigmatism and measuring the effect of the adjustment. The sub method 1068 may include the step 1172 of testing if the number 1060 of Hartmann spots has increased. If the number 1060 of Hartmann spots has increased, then the sub-method 1068 moves on to step 874-1 of setting the control value A to At, and then repeating steps 878-1, the adjustment sub-method 1127 and the test 1172. If the number 1060 of Hartmann spots does not increase, then the sub-method 1068 moves onto a step 1276-2. In the step 1276-2, the PC 117 and/or controller 116 checks if this is the first time step 878-1 has been performed since the sub-method 1068 has started. If the answer to step 1276-2 is yes then the sub-method 1064 may move on to step 880-1, described below.

If the answer to step 1276-2 is no then the sub-method 1068 may move on to a step 870-3 in which the PC 117 and/or controller 116 calculate the temporary control data At based on equation (5) which is similar to step 870-2. After the temporary control value At is calculated, the sub-method 1068 may then move onto sub-method 1127 of adjusting the focus and/or astigmatism measuring the effect of the adjustment. The sub method 768 may include the step 1172 of testing if the number 1060 of Hartmann spots has increased. If the number 1060 of Hartmann spots has increased, then the sub-method 1068 moves on to step 874-1 of setting the control value A to At, and then repeating steps 870-3, the adjustment sub-method 1127 and the test 1172. If the number 1060 of Hartmann spots does not increase, then the sub-method 1068 moves onto a step 880-1. In the step 880-1 the PC 117 and/or controller 116 decides the initial focus setting by resending the old control data A as in step 636 to the ophthalmoscope 100, and the ophthalmoscope 100 readjusts the focus based on the old control data A as in step 638-1.

Method 8

Figure 13:
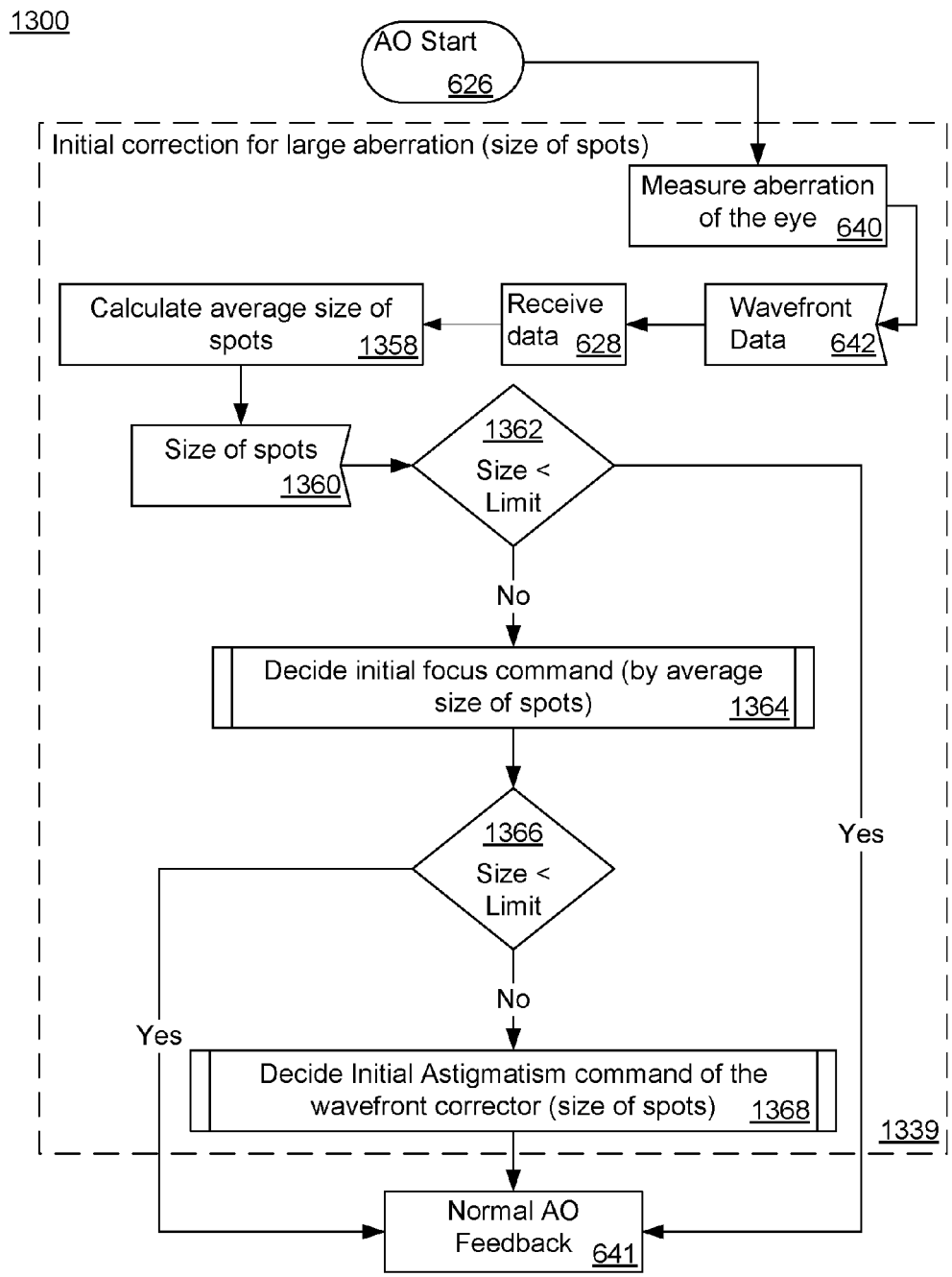
FIG. 13 is an illustration of a method that may be implemented in an embodiment.

FIG. 13 is an illustration of another method 1300 for operating an ophthalmoscope 100 that uses adaptive optics. Method 1300 is similar to method 700, except that the metric used to make focusing decision is different.

After receiving instructions to start the adaptive optics subroutine the method 1300 goes into the first section 1339 of the method 1300 and goes on to the step 640 that includes measuring the aberration of the eye 111 with the wavefront sensor 115 to produce wavefront data 642. The PC 117 or the controller 116 may then receive the wavefront data 642 in a step 628.

In a step 1358, the PC 117 and/or the controller 116 may calculate data 1360 that represents the size of the Hartmann spots 324 in the wavefront data 642. In a step 1362, the PC 117 and/or the controller 116 may compare the size 1360 of the Hartmann spots to a limit. In an alternative, the controller may calculate multiple statistical values based on the size of the Hartman spots (Max, Min, mean, median, variance, deviation, etc.) and compare these to multiple thresholds.

If the size 1360 of the Hartmann spots is less than the limit, then the method 1300 goes on to the Normal AO feedback method 641. If the number 1360 of Hartmann spots is not less than the limit, then the method 1300 goes on to decide an initial focus command in a step 1364 based on the size 1360 of the Hartmann spots. Step 1364 is similar to 764 except that the size of spots is used in the calculation instead of the intensity of spots.

After the focus is adjusted in step 1364, the PC 117 and/or the controller 116 may recalculate the size 1360 of the Hartmann spots 1060 based on new data as obtained in steps 640, 628, and 1358 and re-compare the new size of the spots to a limit in a step 1366. The limit in the step 1366 may be different from the limit in step 1362. If the size 1360 of the Hartmann spots is less than the limit, then the method 1000 goes on to the Normal AO feedback method 641. If the size 1360 is not less than the limit, then the PC 117 and/or the controller 116 calculates a second set of control data which is sent to the ophthalmoscope 100 to send to the wavefront adjustment device 108 or other optical element to compensate for an estimated initial astigmatism based on the size 1360 of the Hartman spots in a step 1368. After the wavefront adjustment device 108 or other optical components compensates for the estimated astigmatism of the subject 111 in step 1368 the method goes on to Normal AO feedback method 641.

Sub-Method 9

Figure 14:
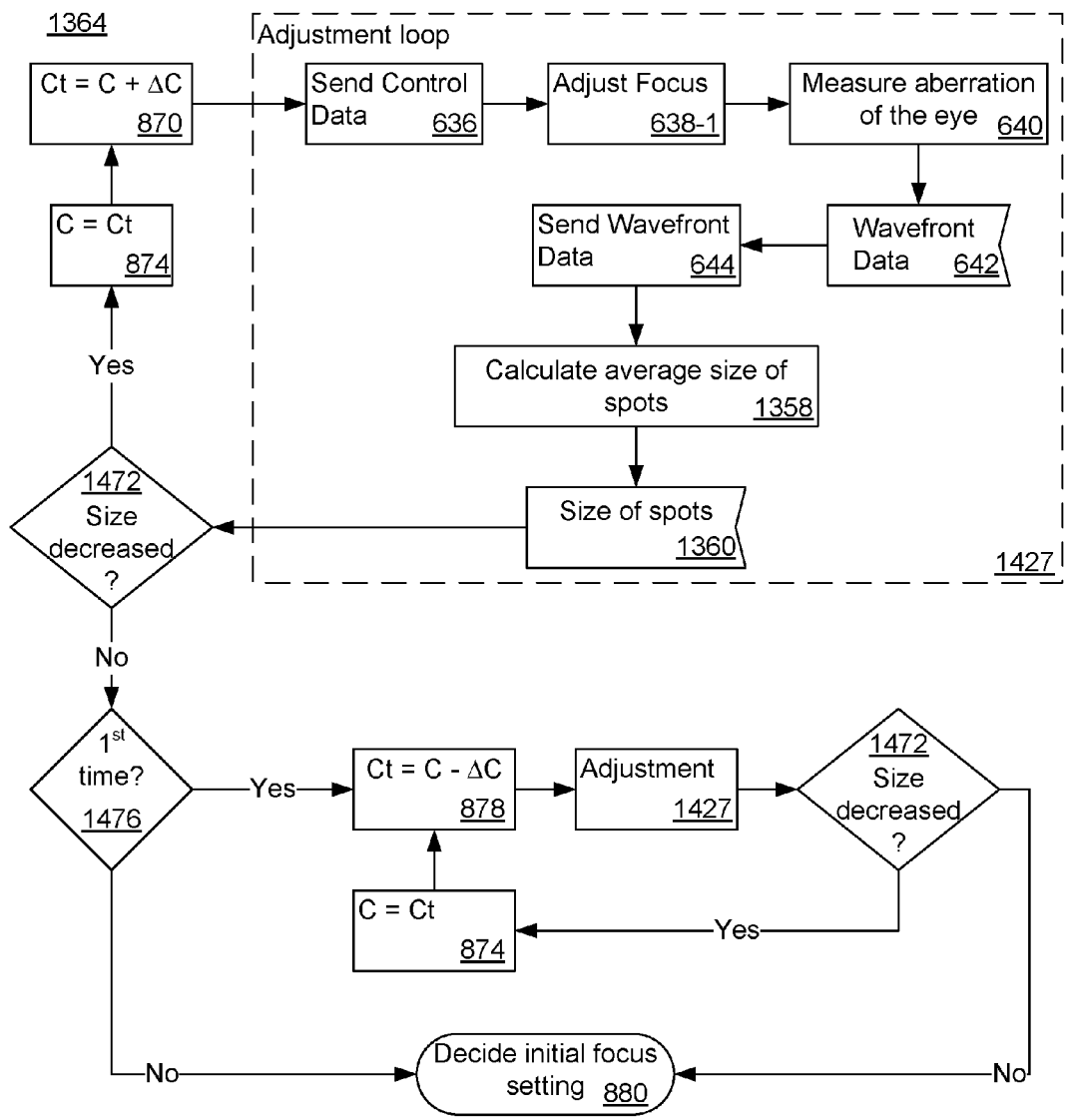
FIG. 14 is an illustration of a portion of a method that may be implemented in an embodiment.

FIG. 14 is an illustration of the sub-method 1364 for deciding the initial focus command. A step 870 may include the PC 117 and/or controller 116 calculating a temporary control data (Ct) value based on equation (1). After the Ct value is calculated, the sub-method 1364 may enter another sub-method 1427 which is an adjustment loop for adjusting the focus and measuring the effect of that adjustment. Adjustment loop 1427 is substantially similar to adjustment loop 827. A step 636 may include sending the control data Ct. In the step 638-1 the focus is adjusted based on the control data Ct.

After the focus is adjusted in step 638-1 the sub-method 764 may include the step 640 of measuring the aberration of the eye 111 to produce wavefront data 642. The sub-method 1364 may include the step 644 of sending the wavefront data 644. In a step 1358, the PC 117 and/or the controller 116 may estimate the size 1360 of the Hartmann spots 324 in the wavefront data 642. Thus, the adjustment loop 1427 may include the steps 636, 640, 644, and 1358 or other methods for adjusting the state of the ophthalmoscope 100 and measuring the impact of that adjustment.

The sub method 1364 may include a step 1472 of testing if the size 1360 of Hartmann spots 324 has decreased. If the size 1360 has decreased, then the sub-method 1364 moves on to step 874 of setting the control value C to Ct, and then repeating the step 870, the adjustment loop 1427, and the decision step 1472. If the size 1360 does not increase, then the sub-method 1364 moves onto a step 1476. In the step 1476, the PC 117 and/or controller 116 checks if this is the first time step 1472 has been performed since the sub-method 1364 has started. If the answer to step 1476 is no then the sub-method 1364 may move on to step 880, described above. If the answer to step 1476 is yes then the sub-method 1364 may move on to a step 878 of calculating the temporary control data (Ct) value based on equation (2).

After step 878, then the sub-method 1364 may go on to perform adjustment sub-method 1427 which was described above. If the size 1360 has decreased, then the sub-method 1364 moves on to step 874 of setting the control value C to Ct, and then repeating steps 878, adjustment sub-method 1427, and step 1472. If the size 1460 does not decrease, then the sub-method 1364 moves onto a step 880. In the step 880, the initial focus is set by resending the old control data C as in step 636 to the ophthalmoscope 100, and the ophthalmoscope 100 readjusts the focus based on the old control data C as in step 638-1.

Sub-Method 10

Figure 15:
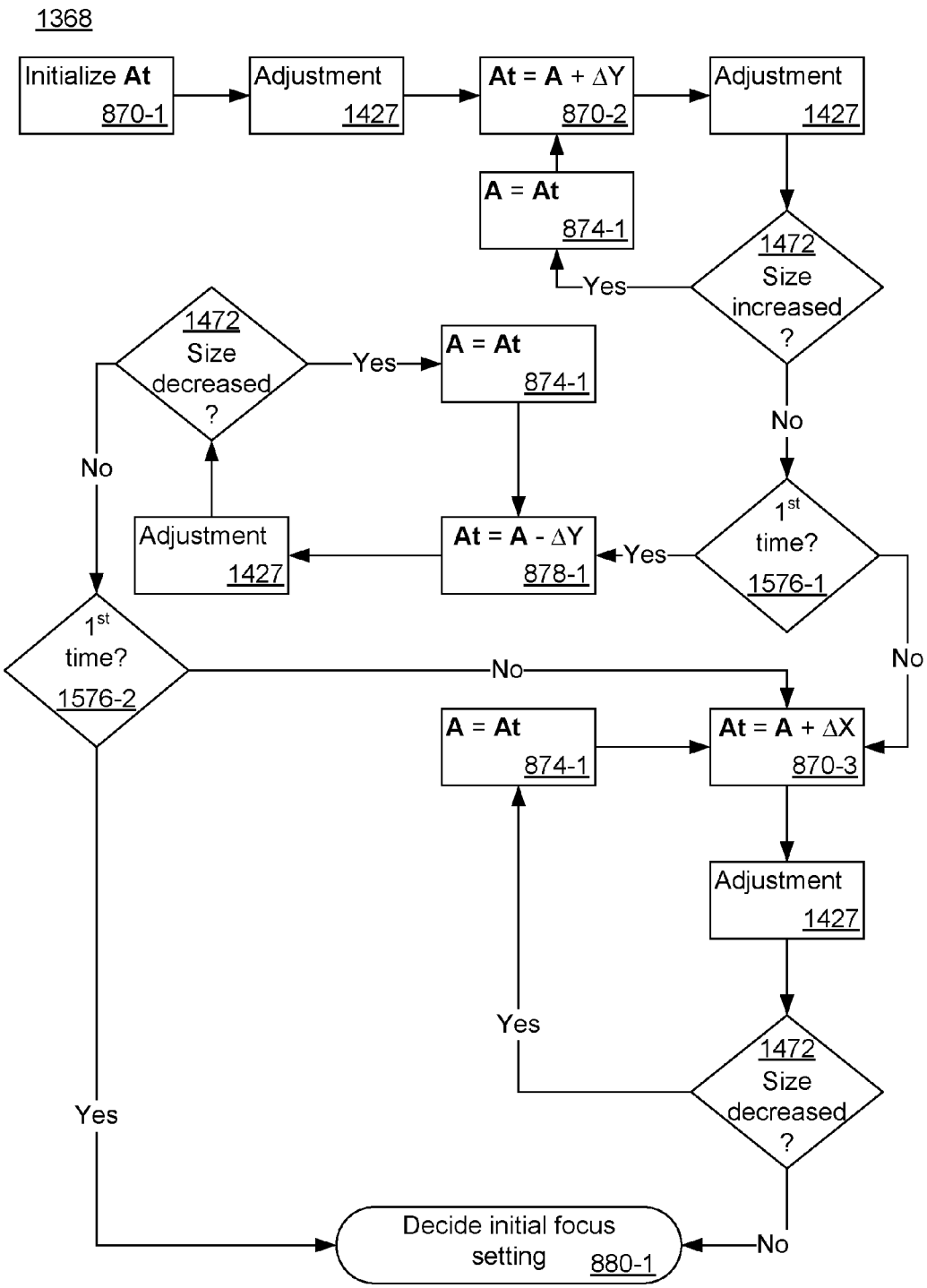
FIG. 15 is an illustration of a portion of a method that may be implemented in an embodiment.

FIG. 15 is an illustration of a sub-method 1368 for deciding the initial focus command which corrects for the astigmatism. The sub-method 1368 may include a step 870-1 of initializing the temporary control data At. The sub-method 1368 may then move onto the sub-method 1427 of adjusting the focus and measuring the impact of the adjustment. After which the method may move on to step 870-2 in which the axis is adjusted according to equation (3). After the temporary control value At is calculated the sub-method 1368 may then move onto sub-method 1427 of adjusting the focus and/or astigmatism and measuring the effect of the adjustment. The sub method 1368 may include the step 1472 of testing if the size 1360 of the Hartmann spots has decreased. If the size 1360 has decreased, then the sub-method moves on to step 874-1 of setting the control value A to At, and then repeating steps 870-2, the adjustment sub-method 1427 and the test 1472. If the size 1360 does not increase, then the sub-method 1368 moves onto a step 1576-1. In the step 1576-1, the PC 117 and/or controller 116 checks if this is the first time step 870-2 has been performed since the sub-method 1368 has started. If the answer to step 1576-1 is no then the sub-method 1368 may move on to step 870-3, described below.

If the answer to step 1576-1 is yes then the sub-method 1368 may move on to a step 878-1 in which the PC 117 and/or controller 116 calculate the temporary control data At based on equation (4). After the temporary control value At is calculated the sub-method 1368 may then move onto sub-method 1427 of adjusting the focus and/or astigmatism and measuring the effect of the adjustment. The sub method 1368 may include the step 1472 of testing if the size 1360 has decreased. If the size 1360 has decreased, then the sub-method 1368 moves on to step 874-1 of setting the control value A to At, and then repeating steps 878-1, the adjustment sub-method 1427 and the test 1472. If the size 1360 does not decrease, then the sub-method 1368 moves onto a step 1576-2. In the step 1576-2, the PC 117 and/or controller 116 checks if this is the first time step 878-1 has been performed since the sub-method 1368 has started. If the answer to step 1576-2 is yes then the sub-method 1368 may move on to step 880-1, described below.

If the answer to step 1576-2 is no then the sub-method 1368 may move on to a step 870-3 in which the PC 117 and/or controller 116 calculate the temporary control data At based on equation (5) which is similar to step 870-2. After the temporary control value At is calculated, the sub-method 1368 may then move onto sub-method 1427 of adjusting the focus and/or astigmatism measuring the effect of the adjustment. The sub method 1368 may include the step 1472 of testing if the size 1360 of Hartmann spots has decreased. If the size 1360 has decreased, then the sub-method 1368 moves on to step 874-1 of setting the control value A to At, and then repeating steps 870-3, the adjustment sub-method 1427 and the test 1472. If the size 1360 does not decrease, then the sub-method 1368 moves onto a step 880-1. In the step 880-1 the PC 117 and/or controller 116 decides the initial focus and/or astigmatism setting by resending the old control data A as in step 636 to the ophthalmoscope 100, and the ophthalmoscope 100 readjusts the focus and/or astigmatism based on the old control data A as in step 638-1.

Controller

Figure 16:
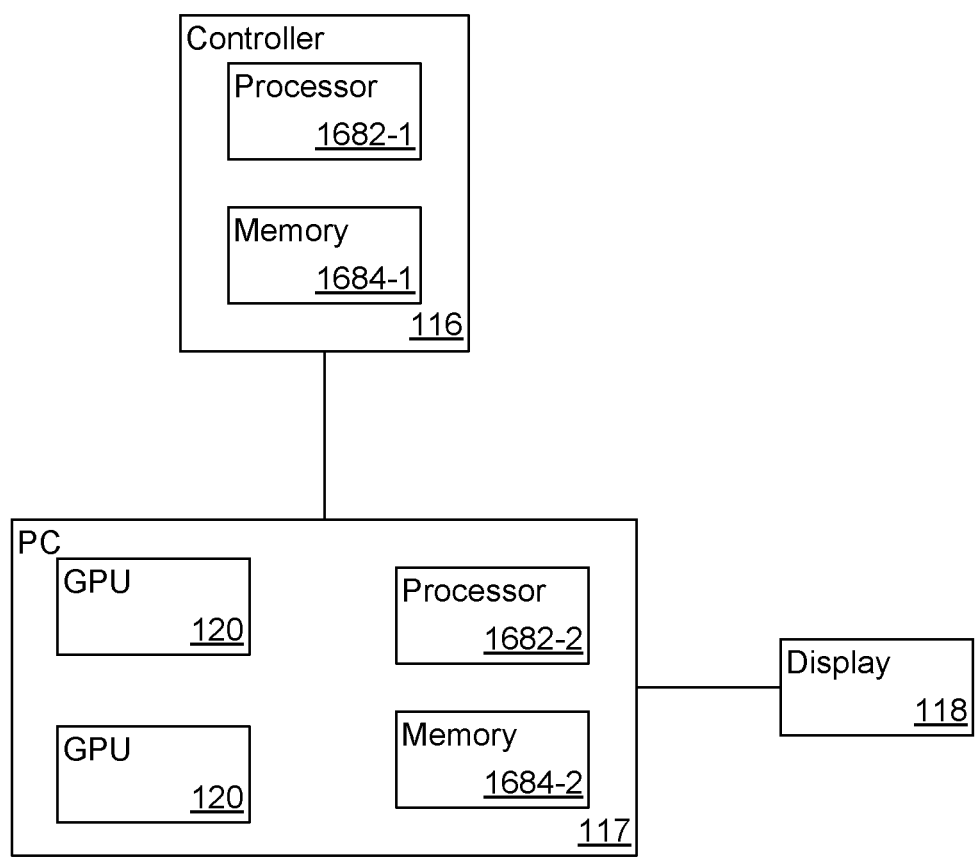
FIG. 16 is an illustration of a controller that may be used in an embodiment.

FIG. 16 is an illustration of the PC 117 and controller 116 that may be used in an embodiment. The controller 116 receives input signals and outputs control signals. The controller 116 may be a general purpose computer, a device specifically designed to controller the ophthalmoscope or measuring instrument, or a hybrid device that uses some custom electronics along with a general purpose computer 117. The input signals and control signals maybe digital signals or analog signals. The controller 116 may include an analog to digital converter (ADC) and a digital to analog converter (DAC). The input signals may include one more signals such as a signal from the wavefront sensor 115, a signal from the detector 114, and one or more signals from one or more other sensors. The control signals may include a first control signal to a wavefront adjustment device 108 and signals to one or more of the scanners 109-1, 109-2. The control signals may include additional signals to other components of the instrument.

The controller 116 includes a processor 1682-1. The processor 1682-1 may be a microprocessor, a CPU, an ASIC, a DSP, and/or a FPGA. The processor 1682-1 may refer to one or more processors that act together to obtain a desired result. The controller 116 may include a memory 1684-1. The memory 1684-1 may store calibration information. The memory 1684-1 may also store software for controlling the ophthalmoscope. The memory 1684-1 may be a form of a non-transitory computer readable storage medium. The non-transitory computer readable storage medium may include, for example, one or more of a hard disk, a random-access memory (RAM), a read only memory (ROM), a distributed storage system, an optical disk (CD, DVD or Blu-Ray Disc, a flash memory device, a memory card, or the like.

The controller 116 may be connected to a computer (PC) 117 via a direct connection, a bus, or via a network. The computer 117 may include input devices such as a keyboard, a mouse, and/or a touch screen. The controller 116 may include input devices such as a keyboard, a mouse, a touch screen, knobs, switches, and/or buttons. The computer 117 may be connected to a display 118. The results of the ophthalmoscope may be presented to a user via the display 118. The tracking software which may be used to implement an embodiment may perform calculations on the controller 116 independently of the PC 117 or with the help of the PC 117. The PC may include a processor 1682-2, a memory 1684-2. The PC may also include one or more GPUs 120

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

What is claimed is:

1. A method for controlling an optical-image pickup apparatus configured to radiate measurement light onto a subject, to measure a wavefront aberration generated at the subject with a wavefront measurement device, to correct the aberration with a wavefront correction device, and to acquire an optical image of the subject, the method comprising:
   receiving a first set of quality data that is representative of a quality of wavefront data, wherein the wavefront data is an estimation of wavefront aberrations generated at the subject;
   comparing the first set of quality data to a first threshold;
   in a first case wherein the comparison of the first set of quality data indicates that the wavefront data is of sufficient quality then performing normal adaptive optics feedback comprising:
      sending a first set of control information to the optical-image pickup apparatus instructing the optical-image pickup apparatus to compensate for aberrations based on an estimated shape of the wavefront based on the received wavefront data; and
      re-estimating the shape of the wavefront based on re-acquired wavefront data and sending a new first set of control information to the optical-image pickup apparatus instructing the optical-image pickup apparatus to compensate for aberrations based on the re-estimated shape of the wavefront; and
   in a second case wherein the comparison of the first set of quality data indicates that the wavefront data is not of sufficient quality then performing an initial adjustment comprising:
      sending a second set of control information to the optical-image pickup apparatus instructing the optical-image pickup apparatus to modify the optical path in which measurement light is radiated onto the subject;
      receiving a new first set of quality data, to replace the previously received first set of quality data, that is based on new wavefront data after the optical path has been modified; and
      re-comparing the new first set of quality data to the first threshold;
   in a third case wherein the comparison of the first set of quality data that is based on the new wavefront data indicates that the new wavefront data is of sufficient quality then performing the normal adaptive optics feedback in which the optical path has been adjusted based on the second set of control information; and
   in a fourth case wherein the comparison of the first set of quality data that is based on the new wavefront data indicates that the new wavefront data is not of sufficient quality then re-performing the initial adjustment based on a new second set of control information.

2. The method according to claim 1, wherein before receiving the first set of quality data the wavefront correction unit compensates for the known optical aberrations based on optical prescription data associated with the subject.

3. The method according to claim 1, wherein modifying the optical path include adjusting a position of a second correction unit other than the wavefront correction unit.

4. The method according to claim 3, wherein:
   a second correction unit includes as least one or more focusing optical components selected from a group including a lens and a mirror; and
   the second set of control information includes instructions for the optical-image pickup apparatus to move the at least one or more focusing optical components.

5. The method of claim 1, wherein the wavefront correction device is one of a deformable mirror or a spatial light phase modulator.

6. The method of claim 5 wherein the wavefront measurement device is a Shack-Hartman sensor that detects a plurality of Hartmann spots.

7. The method of claim 6 wherein the first set of quality data is based on a numerical count of the plurality of Hartmann spots.

8. The method of claim 6 wherein the first set of quality data is based on a plurality of diameters of the plurality of Hartmann spots.

9. The method of claim 6 wherein the first set of quality data is based on signal intensity data of the plurality of Hartmann spots.

10. The method of claim 1, wherein the normal adaptive optics feedback is done repeatedly so as to form a feedback loop.

11. The method of claim 10, further comprises:
   controlling the image pickup apparatus so as to acquire the optical image of the subject by scanning a spot in parallel with continuous use of the normal adaptive optics feedback.

12. The method of claim 1, wherein the initial adjustment is performed repeatedly until the comparison of the first set of quality data with the first threshold indicates that the wavefront data is of sufficient quality and controlling the image pickup apparatus so as to acquire the optical image of the subject by scanning a spot in parallel with continuous use of the normal adaptive optics feedback after the comparison of the first set of quality data with the first threshold indicates that the wavefront data is of sufficient quality.

13. The method of claim 1, wherein:
   the initial adjustment is performed repeatedly, wherein the initial adjustment includes:

a first part of modifying the optical path by adjusting a position of one or more focusing optical components to change the focus until the comparison of the first set of quality data with the first threshold indicates that the wavefront data is of sufficient quality; and a second part, of modifying the optical path by adjusting a position of one or more focusing optical components to change the astigmatism until the comparison of the first set of quality data with a second threshold indicates that the wavefront data is of sufficient quality; and controlling the image pickup apparatus so as to acquire the optical image of the subject by scanning a spot in parallel with continuous use of the normal adaptive optics feedback after the comparison of the first set of quality data with the first threshold and the second threshold indicates that the wavefront data is of sufficient quality.

14. The method of claim 1, wherein:

the first set of quality data includes multiple elements which represent different qualitative aspects of the wavefront data;

the first threshold include multiple elements which provide different thresholds for different qualitative aspects of the wavefront data; and comparing the first set of quality data to the first threshold includes comparing those elements of the first set of quality data associated with particular qualitative aspects of the wavefront data with thresholds associated with those qualitative aspects of the wavefront data.

15. A non-transitory computer readable medium encoded with instructions for controlling an optical-image pickup apparatus configured to radiate measurement light onto a subject, to measure a wavefront aberration generated at the subject with a wavefront measurement device, to correct the aberration with a wavefront correction device, and to acquire an optical image of the subject, the instructions comprising:

receiving a first set of quality data that is representative of a quality of wavefront data, wherein the wavefront data is an estimation of wavefront aberrations generated at the subject;

comparing the first set of quality data to a first threshold;

in a first case wherein the comparison of the first set of quality data indicates that the wavefront data is of sufficient quality then performing normal adaptive optics feedback comprising:

sending a first set of control information to the optical-image pickup apparatus instructing the optical-image pickup apparatus to compensate for aberrations based on an estimated shape of the wavefront based on the received wavefront data; and re-estimating the shape of the wavefront based on re-acquired wavefront data and sending a new first set of control information to the optical-image pickup apparatus instructing the optical-image pickup apparatus to compensate for aberrations based on the re-estimated shape of the wavefront; and in a second case wherein the comparison of the first set of quality data indicates that the wavefront data is not of sufficient quality then performing an initial adjustment comprising:

sending a second set of control information to the optical-image pickup apparatus instructing the optical-image pickup apparatus to modify the optical path in which measurement light is radiated onto the subject;

receiving a new first set of quality data, to replace the previously received first set of quality data, that is based on new wavefront data after the optical path has been modified; and re-comparing the new first set of quality data to the first threshold;

in a third case wherein the comparison of the first set of quality data that is based on the new wavefront data indicates that the new wavefront data is of sufficient quality then performing the normal adaptive optics feedback in which the optical path has been adjusted based on the second set of control information; and in a fourth case wherein the comparison of the first set of quality data that is based on the new wavefront data indicates that the new wavefront data is not of sufficient quality then re-performing the initial adjustment based on a new second set of control information.

16. A controller for controlling an optical-image pickup apparatus configured to radiate measurement light onto a subject, to measure a wavefront aberration generated at the subject with a wavefront measurement device, to correct the aberration with a wavefront correction device, and to acquire an optical image of the subject, the controller comprising:

a processor; and memory;

the processor receiving a first set of quality data that is representative of a quality of wavefront data, wherein the wavefront data is an estimation of wavefront aberrations generated at the subject;

the processor comparing the first set of quality data to a first threshold;

in a first case wherein the comparison of the first set of quality data indicates that the wavefront data is of sufficient quality then the processor performing normal adaptive optics feedback comprising:

the processor sending a first set of control information to the optical-image pickup apparatus instructing the optical-image pickup apparatus to compensate for aberrations based on an estimated shape of the wavefront based on the received wavefront data; and the processor re-estimating the shape of the wavefront based on re-acquired wavefront data and sending a new first set of control information to the optical-image pickup apparatus instructing the optical-image pickup apparatus to compensate for aberrations based on the re-estimated shape of the wavefront; and in a second case wherein the comparison of the first set of quality data indicates that the wavefront data is not of sufficient quality then the processor performing an initial adjustment comprising:

the processor sending a second set of control information to the optical-image pickup apparatus instructing the optical-image pickup apparatus to modify the optical path in which measurement light is radiated onto the subject;

the processor receiving a new first set of quality data, to replace the previously received first set of quality data, that is based on new wavefront data after the optical path has been modified; and the processor re-comparing the new first set of quality data to the first threshold;

in a third case wherein the comparison of the first set of quality data that is based on the new wavefront data indicates that the new wavefront data is of sufficient quality then the processor performing the normal adaptive optics feedback in which the optical path has been adjusted based on the second set of control information; and in a fourth case wherein the comparison of the first set of quality data that is based on the new wavefront data indicates that the new wavefront data is not of sufficient quality then the processor re-performing the initial adjustment based on a new second set of control information.

17. An apparatus comprising:
the optical-image pickup apparatus; and
the controller of claim 16.

18. A method for controlling an optical-image pickup apparatus configured to radiate measurement light onto a subject, to measure a wavefront aberration generated at the subject with a wavefront measurement device, to correct the aberration with a wavefront correction device, and to acquire an optical image of the subject, the method comprising:

receiving a set of quality data that is representative of a quality of wavefront data, wherein the wavefront data is an estimation of wavefront aberrations generated at the subject;

comparing the set of quality data to a threshold in a state before normal adaptive optics feedback is started in the optical-image pickup apparatus;

in a case wherein the comparison of the set of quality data indicates that the wavefront data is of sufficient quality then starting the normal adaptive optics feedback comprising:
  receiving the wavefront data; and
  sending a set of control information to the optical-image pickup apparatus instructing the optical-image pickup apparatus to compensate for the aberrations based on the received wavefront data; and in a case wherein the comparison of the set of quality data indicates that the wavefront data is not of sufficient quality then sending a set of control information to the optical-image pickup apparatus instructing the optical-image pickup apparatus to modify the optical path in which measurement light is radiated onto the subject.

19. The method according to claim 18, wherein modifying the optical path includes adjusting a position of a second correction unit, other than the wavefront correction unit, to control light radiated by or received by the optical-image pickup apparatus, the second correction unit including as least one or more focusing optical components selected from a group including a lens and a mirror.

20. The method according to claim 19, wherein the wavefront correction device is one of a deformable mirror or a spatial light phase modulator.

21. The method according to claim 20 wherein the wavefront measurement device is a Shack-Hartman sensor that detects a plurality of Hartmann spots.

22. The method according to claim 21 wherein the set of quality data is based on signal intensity data of the plurality of Hartmann spots.

23. The method of claim 18, further comprises:
controlling the image pickup apparatus so as to acquire the optical image of the subject by scanning a spot in parallel with continuous use of the normal adaptive optics feedback.

24. A controller for controlling an optical-image pickup apparatus configured to radiate measurement light onto a subject, to measure a wavefront aberration generated at the subject with a wavefront measurement device, to correct the aberration with a wavefront correction device, and to acquire an optical image of the subject, the controller comprising:
a processor; and
a memory storing a program of instructions that when executed by the processor causes the processor to:
receive a set of quality data that is representative of a quality of wavefront data, wherein the wavefront data is an estimation of wavefront aberrations generated at the subject;
compare the set of quality data to a threshold in a state before normal adaptive optics feedback is started in the optical-image pickup apparatus;
in a case wherein the comparison of the set of quality data indicates that the wavefront data is of sufficient quality then start the normal adaptive optics feedback comprising:
  receiving the wavefront data; and
  sending a set of control information to the optical-image pickup apparatus instructing the optical-image pickup apparatus to compensate for the aberrations based on the received wavefront data; and
in a case wherein the comparison of the set of quality data indicates that the wavefront data is not of sufficient quality then send a set of control information to the optical-image pickup apparatus instructing the optical-image pickup apparatus to modify the optical path in which measurement light is radiated onto the subject.

25. An apparatus comprising:
the optical-image pickup apparatus; and
the controller of claim 24.

* * * * *